(12) United States Patent
Nayak

(10) Patent No.: US 8,506,933 B2
(45) Date of Patent: Aug. 13, 2013

(54) METHODS OF DETECTING A NEUROLOGICAL CONDITION VIA ANALYSIS OF CIRCULATING PHAGOCYTES

(75) Inventor: Ramesh C. Nayak, Tucson, AZ (US)

(73) Assignee: MSDx, Inc., Tucson, AZ (US)

( * ) Notice: Subject to any disclaimer, the term of this patent is extended or adjusted under 35 U.S.C. 154(b) by 775 days.

(21) Appl. No.: 12/325,035

(22) Filed: Nov. 28, 2008

(65) Prior Publication Data
US 2010/0055722 A1 Mar. 4, 2010

Related U.S. Application Data

(60) Provisional application No. 60/991,594, filed on Nov. 30, 2007, provisional application No. 61/007,728, filed on Dec. 14, 2007, provisional application No. 61/020,820, filed on Jan. 14, 2008, provisional application No. 61/042,407, filed on Apr. 4, 2008.

(51) Int. Cl.
| | |
|---|---|
| *A61B 5/1477* | (2006.01) |
| *C07K 1/02* | (2006.01) |
| *C07K 14/47* | (2006.01) |
| *G01N 33/487* | (2006.01) |
| *G01N 33/49* | (2006.01) |
| *G01N 33/50* | (2006.01) |

(52) U.S. Cl.
USPC ............... 424/9.1; 435/4; 435/7.21; 530/350; 530/388.73

(58) Field of Classification Search
None
See application file for complete search history.

(56) References Cited

U.S. PATENT DOCUMENTS

| | | | |
|---|---|---|---|
| 5,578,709 | A | 11/1996 | Woiszwillo |
| 5,874,399 | A | 2/1999 | Samal |
| 6,368,785 | B1 | 4/2002 | Ranby |
| 6,589,746 | B1 | 7/2003 | Zemlan |
| RE38,431 | E | 2/2004 | Miekka et al. |
| 2003/0161826 | A1 | 8/2003 | Arnason et al. |
| 2004/0019118 | A1 | 1/2004 | Iqbal et al. |
| 2007/0048264 | A1 | 3/2007 | Kindsvogel et al. |
| 2007/0072295 | A1 | 3/2007 | Slukvin et al. |
| 2007/0196337 | A1 | 8/2007 | Trapani et al. |
| 2008/0183395 | A1 | 7/2008 | Bevilacqua et al. |

FOREIGN PATENT DOCUMENTS

| | | |
|---|---|---|
| WO | 99/45393 A1 | 9/1999 |
| WO | 02/03073 A1 | 1/2002 |
| WO | 2005/080985 A2 | 9/2005 |

OTHER PUBLICATIONS

Galimberti et al., Neurobiology of Aging, 27:1763-1768, 2006, epublished Nov. 22, 2005.*
Bomprezzi et al., Hum Mol Genetics, 12(17): 2191-2199, 2003.*
Streit et al., J Neuroinflam, 1:14, 2004.*
Bentivoglio et al., Brain Research Reviews, 66:152-173, 2011.*
Iglesias et al., J Neuroimmunology, 150:163-177, 2004.*
Singh et al. J Neurol Sci., 258:52-59, 2007.*
Jin et al., J Leukocyte Biol., 87:779-789. 2010.*
Kurne et al., Rheumatolog Int., 29:1249-1353, 2009.*
Rosner et al., Arthritis and Rheumatism, 25(6):612-617, 1982.*
Arnold et al.; Increase in Perforin-positive Peripheral Blood Lymphocytes in Extrinsic and Intrinsic Asthma; Am J Respir Crit Care Med.; vol. 161; p. 182-186; 2000.
Kapaki et al.; Increased Cerebrospinal Fluid Tau Protein in Multiple Sclerosis; Eur Neruol 2000; 43:228-232.
Körner et al.; Molecular Characteristics of Serum Visfatin and Differential Detection by Immunoassays; Journal of Clinical Endocrinology & Metabolism; vol. 92; p. 4783-4791; Sep. 18, 2007.
Dahmen et al.; Elevated Peripheral Visfatin Levels in Narcoleptic Patients; PLoS One; www.plosone.org; vol. 3; p. e2980; Aug. 20, 2008.
Haider et al.; Exercise Traling Lowers Plasma Visfatin Concentrations in Patients with Type 1 Diabetes; Journal of Clinical Endocrinology & Metabolism; vol. 91; p. 4702-4704; Aug. 8, 2006.
Pajvani et al.; Structure-Function Studies of the Adipocyte-secreted Hormone Acrp30/Adiponectin; Journal of Biological Chemistry; vol. 278; p. 9073-9085; Mar. 14, 2003.
Lu et al; Elevated Visfatin/Pre-B-cell Colony-enhancing Factor Plasma Concentration in Ischemic Stroke; Journal of Stroke and Cerebrovascular Diseases; vol. 18, No. 5; p. 354-359; Oct. 2009.
Rukavina et al; Age-Related Decline of Perforin Expression in Human Cytotoxic T Lymphocytes and Natural Killer Cells; Blood Journal; vol. 92; p. 2410-2420; Oct. 1, 1998.
Bartosik-Psujek, Halina et al; Tau protein and 14-3-3 are elevated in the cerebrospinal fluid of patients with multiple sclerosis and correlate with intrahecal synthesis of IgG; Journal of Neurology; vol. 251; No. 4; Apr. 2004; pp. 414-420; XP002672838; ISSN: 0340-5354.
Guimares et al.; Tau protein seems not to be a useful routine clinical marker of axonal damage in multiple sclerosis; Multiple Sclerosis 2006; 12: 354-356.
Rezai-Zadeh, Kavon et al.; CNS Infiltration of Peripheral Immune Cells: D-Day for Neurodegenerative Disease?; J Neuroimmune Pharmacol (2009) 4:462-475.
Batrakova, Elena V. et al.; A Macrophage—Nanozyme Deliver System for Parkinson's Disease; NIH Public Access; Bioconjug Chem. 2007; 18(5): 1498-1506.
Biju, KC et al.; Macrophage-mediated GDNF Delivery Protects Against Dopaminergic Neurodegeneration: A Therapeutic Strategy for Parkinson's Disease; The American Society of Gene & Cell Therapy; www.moleculartherapy.org; vol. 18; No. 8; 1536-1544; Aug. 2010.
Joly, Sandrine et al.; Cooperative Phagocytes—Resident Microglia and Bone Marrow Immigrants Remove Dead Photoreceptors in Retinal Lesions; The American Journal of Pathology 2009; vol. 174; No. 6; 2310-2323.

* cited by examiner

*Primary Examiner* — Daniel E Kolker
*Assistant Examiner* — Stacey N MacFarlane

(57) ABSTRACT

The present invention features methods of monitoring or detecting a neurological or inflammatory condition in a patient. The method comprises (1) obtaining from the patient a fluid sample from outside of a brain tissue of the patient, wherein the fluid sample contains a circulating phagocyte, and (2) detecting for one or more biomarkers (e.g., a panel of biomarkers) inside the phagocyte, wherein the biomarker is associated with the respective neurological or inflammatory condition.

1 Claim, No Drawings

METHODS OF DETECTING A NEUROLOGICAL CONDITION VIA ANALYSIS OF CIRCULATING PHAGOCYTES

CROSS REFERENCE

This application claims priority to U.S. provisional application Ser. No. 60/991,594 filed Nov. 30, 2007; U.S. provisional application Ser. No. 61/007,728 filed Dec. 14, 2007; U.S. provisional application Ser. No. 61/020,820 filed Jan. 14, 2008; U.S. provisional application Ser. No. 61/042,407 filed Apr. 4, 2008; the entire disclosures of which are incorporated herein by reference in its entirety.

BACKGROUND OF THE INVENTION

Multiple Sclerosis (MS) is predominantly a disease of women of northern European origin and afflicts up to three million people worldwide. In the United States it is estimated that 400,000 people are affected. It is thought to be an autoimmune disorder and typically strikes young adults, causing a wide variety of symptoms that are often mistaken for other diseases. These symptoms stem from disruption of the central nervous system (CNS) and may include blurred or double vision; weakness in the arms or legs; changes or difficulties in balance, coordination and gait; bladder and/or bowel dysfunction; and emotional disturbances. Each patient may present a little differently and there may have been episodes in the past which were barely noticed by the patient at the time. It is difficult to firmly diagnose MS, especially if there has been only one symptomatic episode. This leaves patients and their doctors waiting months or years for a relapse to confirm that the symptoms are due to MS.

MS is a demyelinating disease, where myelin, the insulating layer on nerve fibers, is destroyed in the CNS, which consists of the brain, optic nerves, and spinal column. There is an accompanying inflammatory response and the blood brain barrier (BBB) is breached. Axon damage can occur and the optic nerve is commonly affected. Myelin damage makes it more difficult for nerves to transmit impulses, leading to symptoms of MS. The diagnostic McDonald Criteria (1) were revised in 2005 to include magnetic resonance imaging (MRI) criteria of different types of lesions of the brain and spinal cord in the diagnosis of MS. Prognosis is difficult to determine, and many brain lesions do not necessarily correlate with severity of disease. There are medications available to alleviate some symptoms and a few others to modify and hopefully delay the onset or severity of relapses of MS.

The most common form of MS is relapsing-remitting multiple sclerosis (RRMS), which is characterized by symptomatic episodes separated in time, with partial or complete recovery of an apparently normal state between relapses. It often converts to secondary progressive MS after several years, where there is a steady worsening of symptoms. A minority of patients have Primary Progressive MS which presents as a continuous slow worsening of the disease state. An even smaller minority of patients is diagnosed with Progressive-Relapsing MS, where in contrast to RRMS, there is a continuous worsening of their condition between acute episodes. A first episode is referred to as Clinically Isolated Syndrome (CIS) pending a more certain diagnosis of MS corresponding to clinical signs and/or brain lesions visualized by MRI, or possibly a spinal tap to check for immunoglobulin oligoclonal bands (OCB) in the cerebral spinal fluid (CSF). None of these diagnostic methods is 100% specific. (2). Its drawbacks include the expense and the fact that a patient must wait one to three months between scans to determine if new lesions have formed during the intervening period. There is a clear need for identification of a biomarker or set of biomarkers that indicate presence and/or severity of disease for MS patients. A simple blood test would be ideal for diagnosing MS, however at this time, no commercial blood test exists.

Early diagnosis of MS is thought to be increasingly important, as much of the damage occurs early in the disease process. The earlier the diagnosis, the earlier disease-modifying treatment can begin and progression of the disease and associated disability can hopefully be slowed.

The present invention features a method of detecting multiple sclerosis or a risk of multiple sclerosis. The method comprises detecting a multiple sclerosis-associated biomarker, e.g., an antigen, wherein detecting an elevated level of such multiple sclerosis-associated biomarker indicates the presence of multiple sclerosis or a risk of multiple sclerosis.

SUMMARY OF THE INVENTION

The present invention features a method of monitoring or detecting a neurological condition in a patient, the method comprises (a) obtaining from a patient a fluid sample from outside of a brain tissue of the patient, the fluid sample contains a circulating phagocyte; and (b) detecting a biomarker associated with the neurological condition in the phagocyte.

Further, the present invention features a method of monitoring or detecting multiple sclerosis (or a risk of multiple sclerosis) in a patient, the method comprises (a) obtaining from the patient a fluid sample from outside of a brain tissue of the patient, the fluid sample contains a circulating phagocyte; and (b) detecting a multiple sclerosis-associated biomarker in the phagocyte.

Still further, the present invention features a method of monitoring or detecting an inflammatory condition in a patient, said method comprising (a) obtaining from the patient a fluid sample from outside of a brain tissue of the patient, the fluid sample contains a circulating phagocyte; and (b) detecting a biomarker in the phagocyte, wherein the biomarker is associated with the inflammatory condition.

In some embodiments, the monitoring of one of the above conditions is achieved by detecting the level of the respective biomarkers through a time interval. In some embodiments, a decrease in the level of a biomarker through time is an indication that the condition is improving (assuming that the level of biomarker directly correlates with the severity of the condition). In some embodiments, an increased in the level of a biomarker through time is an indication that the condition is improving (assuming that the level of biomarker is inversely correlates with the severity of the condition).

In some embodiments, the detection of the one of the above conditions is achieved by detecting a biomarker that is at a level that is higher than that of a control (assuming that an elevated level of the biomarker relative to that of a control is indicative of a condition—this correlation may be established by routine procedures by one of ordinary skill).

In some embodiments, the detection of the one of the above conditions is achieved by detecting a biomarker that is at a level that is lower than that of a control (assuming that a decreased level of the biomarker relative to that of a control is indicative of a condition—this correlation may be established by routine procedures by one of ordinary skill).

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims. Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

DESCRIPTION OF PREFERRED EMBODIMENTS

Inflammatory Conditions

The present invention features a method of detecting an inflammatory condition. The method comprises obtaining from a patient a fluid sample that contains a peripheral (e.g., circulating) phagocyte, and detecting one or more biomarker, e.g., an antigen, inside a phagocyte of said fluid sample, wherein the biomarker is associated with an inflammatory condition. The fluid obtained does not directly come into contact with the inflamed tissue being detected. For example, there is a barrier between the fluid and the source of the biomarker. In other words, the fluid obtained may have once directly come into contact with the inflamed tissue, but at the time that it is being extracted in accordance with the present invention, it is being separated from the inflamed tissue by a barrier.

As used herein, the term "peripheral" refers to anything outside of brain tissue. For example, a peripheral phagocyte may be obtained from cerebrospinal fluid (CSF). Phagocytes may include monocytes, macrophages, and/or lymphocytes. Such circulating phagocytes may be found in tissues, cells, and/or fluids in the body, for example in blood, peripheral blood mononuclear cells (PBMCs), synovial fluid, cerebrospinal fluid (CSF), central nervous system tissues, synovial fluid, cystic fluid, lymph fluid, ascites, pleural effusion, interstitial fluid, ocular fluids, vitreal fluid, urine the like, or a combination thereof. In some embodiments, the biomarker is an intracellular component. For example, the biomarker may be obtained from within a macrophage. In some embodiments, the macrophage sample is permeabilized. In some embodiments, the macrophage is lysed via various means, e.g., hypertonic solution treatment, detergent solution treatment, mechanical stress, etc.

Also, as used herein, "a fluid that does not directly come into contact with the inflamed tissue" is a fluid that is separated from the inflamed tissue by at least one barrier, e.g., a tissue membrane, a layer of cells, etc.

In some embodiments, one or more biomarkers are detected in the collected fluid sample. For example, a pattern of biomarkers may be detected in the sample. Detecting the biomarker or biomarkers indicates the presence of the inflammatory condition or a risk of the inflammatory condition. In some embodiments, detecting an increased level of the biomarker or biomarkers as compared to the level of the biomarker or biomarkers of a control sample indicates the presence of the inflammatory condition or a risk thereof. Control sample is discussed below. In some embodiments, detecting a decreased level of the biomarker or biomarkers as compared to the level of the biomarker or biomarkers of a control sample indicates the presence of the inflammatory condition or a risk thereof.

In some embodiments, the inflammation condition that may be monitored or detected includes Rheumatoid Arthritis, Systemic Lupus Erythematosis, Shogren's Syndrome, and the like.

In some embodiments, the biomarker(s) is a neural-derived biomarker. However, the biomarker(s) is not limited to neural-derived biomarkers. In some embodiments, one or more biomarkers are detected in the sample, wherein the biomarkers are neural-derived, non-neural-derived biomarkers, or a combination thereof.

The biomarker(s) may be detected using a variety of methods. In some embodiments, the step of detecting the biomarker(s) in the sample may comprise introducing an antibody to the sample, wherein the antibody binds to the biomarker or is specific for the biomarker.

In some embodiments, this method of detecting an inflammatory condition is used in combination with one or more different methods for detecting the inflammatory disease. In some embodiments, this method is used to differentiate between one or more inflammatory conditions.

Neurological Conditions

The present invention also features a method of detecting a neurological condition. The method comprises (1) obtaining from a patient a fluid from outside of the patient's brain tissue, wherein the fluid contains a circulating phagocyte, and (2) detecting a neurological condition-associated protein in the phagocyte. In some embodiments, one or more neurological condition-associated proteins are detected in the sample. The neurological condition-associated protein is associated with the neurological condition Detecting the neurological condition-associated protein indicates the presence of the neurological condition or a risk of the neurological condition.

In some embodiments, detecting an increased level of the neurological condition-associated protein as compared to the level of the neurological condition-associated protein of a control sample indicates the presence of the neurological condition or a risk thereof. In some embodiments, detecting a decreased level of the neurological condition-associated protein as compared to the level of the neurological condition-associated protein of a control sample indicates the presence of the neurological condition or a risk thereof. Control sample is discussed below.

In some embodiments, the neurological condition that may be monitored or detected includes Alzheimer's Disease, Parkinson's Disease, Neuromyelitis Optica, transverse myelitis, Acute and chronic Stroke, and the like.

In some embodiments, the neurological condition-associated protein is derived from a brain source. In some embodiments, the neurological condition-associated protein is derived from a non-brain source. In some embodiments, one or more neurological condition-associated proteins is derived from a brain source, a non-brain source, or a combination thereof.

The neurological condition-associated protein may be present in a circulating phagocyte. Phagocytes may include monocytes, macrophages, and/or lymphocytes, Such circulating phagocytes may be found in tissues, cells, and/or fluids in the body, for example in blood, peripheral blood mononuclear cells (PBMCs), cerebrospinal fluid (CSF), central nervous system tissues, synovial fluid, cystic fluid, lymph fluid, ascites, pleural effusion, interstitial fluid, ocular fluids, vitreal fluid, urine, the like, or a combination thereof. In some embodiments, the neurological condition-associated protein is an intracellular component. For example, the neurological condition-associated protein may be obtained from within a macrophage. In some embodiments, the macrophage sample is permeabilized. In some embodiments, the macrophage is lysed via various means, e.g., hypertonic solution treatment, detergent solution treatment, mechanical stress, etc.

In some embodiments, the step of detecting the neurological condition-associated protein in the sample may comprise introducing an antibody to the sample, wherein the antibody binds to the protein or is specific for the protein.

In some embodiments, this method is used in combination with one or more different methods for detecting the neurological condition. In some embodiments, this method is used to differentiate between one or more neurological conditions.

Multiple Sclerosis

The present invention also features methods of detecting multiple sclerosis or a risk of multiple sclerosis. In some embodiments, the method of the present invention may allow for monitoring, detecting and/or predicting a relapse or a remission of multiple sclerosis. In some embodiments, the method of detecting multiple sclerosis is used in combination with one or more methods of detecting multiple sclerosis. For example, the present methods may be used in conjunction with other modalities to monitor, detect or predicting a relapse or a remission of multiple sclerosis.

The method of detecting multiple sclerosis comprises (1) obtaining from a patient a fluid from outside of the patient's brain tissue, wherein the fluid contains a circulating phagocyte, and (2) detecting a multiple sclerosis-associated biomarker in the phagocyte. In some embodiments, one or more multiple sclerosis-associated proteins is detected in the phagocyte sample. The multiple sclerosis-associated biomarker is associated with multiple sclerosis. Detecting the multiple sclerosis-associated biomarker indicates the presence of multiple sclerosis or a risk of multiple sclerosis.

In some embodiments, detecting an increased level of the multiple sclerosis-associated biomarker as compared to the level of the multiple sclerosis-associated biomarker of a control sample indicates the presence of multiple sclerosis or a risk thereof. In some embodiments, detecting a decreased level of the multiple sclerosis-associated biomarker as compared to the level of the multiple sclerosis-associated biomarker of a control sample indicates the presence of multiple sclerosis or a risk thereof. In some embodiments, detecting an increased level of one class of multiple sclerosis-associated biomarker and a decreased of another class of multiple sclerosis-associated biomarker as compared to the respective level of the multiple sclerosis-associated biomarker of a control sample indicates the presence of multiple sclerosis or a risk thereof.

In some embodiments, the sample is obtained from the mammal immediately following a relapse (e.g., exacerbation of symptoms) before a drug (e.g., a steroid) treatment has begun. In some embodiments, the sample is obtained from the mammal before a relapse. In some embodiments, the sample is obtained during the course of the drug (e.g., steroid) treatment.

The multiple sclerosis-associated biomarker may be present in a circulating phagocyte. Phagocytes may include monocytes, macrophages, and/or lymphocytes. For example, macrophages are a type of monocyte and are phagocytic cells important in both specific cell-mediated immunity and non-specific innate immunity. Circulating phagocytes may be found in tissues, cells, and/or fluids in the body, for example in blood, peripheral blood mononuclear cells (PBMCs), cerebrospinal fluid (CSF), central nervous system tissues, synovial fluid, cystic fluid, lymph fluid, ascites, pleural effusion, interstitial fluid, ocular fluids, vitreal fluid, urine, the like, or a combination thereof. In some embodiments, the neurological condition-associated protein is an intracellular component. For example, the neurological condition-associated protein may be obtained from within a macrophage. In some embodiments, the macrophage sample is permeabilized.

As used herein, a mammal includes a human, a mouse, a rat, a llama, a rabbit, a dog, a primate, a guinea pig, a cat, a hamster, a pig, a chicken, a goat, a horse, or a cow.

In some embodiments, the multiple sclerosis-associated biomarker is a Tau protein (or a fragment thereof) or a Tau protein (or fragment thereof) comprising a phosphorylated residue (e.g., a phosphorylated serine reside, a phosphorylated threonine reside). In some embodiments, the phosphorylated residue is serine 214, serine 235, serine 262, serine 356, serine 396, serine 404, serine 413, serine 46, serine 515, serine 516, serine 519, serine 531, serine 552, serine 610, serine 622, serine 641, serine 713, serine 721, serine 726, serine 730, serine 739, threonine 181, threonine 205, threonine 470, threonine 492, threonine 498, threonine 522, threonine 529, threonine 534, threonine 548, the like, or a combination thereof.

In some embodiments, phosphorylation of Tau can decrease its solubility. In some embodiments, the method of detecting multiple sclerosis comprises detecting a level of insoluble Tau protein in the sample. In some embodiments, an increased level of insoluble Tau protein as compared to a control level of insoluble Tau protein is indicative of multiple sclerosis or a risk thereof.

In some embodiments, the multiple sclerosis-associated biomarker is a protein or a fragment thereof selected from the group consisting of neuroglobin, valosin-containing protein, brain hexokinase, hippocalcin-1, nestin, synaptotagmin, myelin associated glycoprotein, transketolase, NS1 associated protein 1, major vault protein, synaptojanin, enolase, alpha synuclein, glial fibrillary acidic protein, S-100 protein-Neu-N, 26S proteasome subunit 9, annexin A2, annexin A3, annexin A5, annexin A6, annexin A11, ubiquitin activating enzyme ZE1, ubiquitin B precursor, vimentin, glyceraldehyde-3-phosphate dehydrogenase, 13-3-3 protein.

The multiple sclerosis-associated biomarker (e.g., Tau protein or fragment thereof) may be of various lengths. For example, in some embodiments, the multiple sclerosis-associated biomarker consists of between about 5 to 20 amino acids. In some embodiments, the multiple sclerosis-associated biomarker consists of about 20 to 40 amino acids. In some embodiments, the multiple sclerosis-associated biomarker consists of about 40 to 80 amino acids. In some embodiments, the multiple sclerosis-associated biomarker consists of about 80 to 150 amino acids. In some embodiments, the multiple sclerosis-associated biomarker consists of about 150 to 200 amino acids. In some embodiments, the multiple sclerosis-associated biomarker consists of about 200 to 300 amino acids. In some embodiments, the multiple sclerosis-associated biomarker consists of about 300 to 400 amino acids. In some embodiments, the multiple sclerosis-associated biomarker consists of about 400 to 500 amino acids. In some embodiments, the multiple sclerosis-associated biomarker consists of about 500 to 600 amino acids.

The multiple sclerosis-associated biomarker (e.g., Tau protein or fragment thereof) may comprise various regions of the full-length protein. For example, in some embodiments, the multiple sclerosis-associated biomarker comprises the amino-terminus (e.g., N-terminus, NH2-terminus, N-terminal end, amine-terminus). The amino-terminus refers to the amino acid at the end of a protein or polypeptide that has a free amine group (—NH2). In some embodiments, the multiple-sclerosis associated biomarker consists of about the first 15 amino acids. In some embodiments, the multiple-sclerosis associated biomarker consists of about the first 25 amino acids. In some embodiments, the multiple-sclerosis associated biomarker consists of about the first 50 amino acids. In some embodiments, the multiple-sclerosis associated biomarker consists of about the first 75 amino acids. In some embodiments, the multiple-sclerosis associated biomarker consists of about the first 100 amino acids. In some embodiments, the multiple-sclerosis associated biomarker consists of about the first 125 amino acids.

In some embodiments, the multiple-sclerosis associated biomarker or fragment thereof comprises the carboxy-terminus (e.g., C-terminus, COOH-terminus, C-terminal end, carboxyl-terminus). The carboxy-terminus refers to the amino acid at the end of a protein or polypeptide that has a free carboxylic acid group (—COOH). In some embodiments, the multiple-sclerosis associated biomarker consists of about the last 100 amino acids.

Table 1 shows the amino acid sequence of full-length human Tau protein.

1) TABLE 1

| Length (# of Amino Acids) | MW (Daltons) | Amino Acid Sequence | Amino Acids | SEQ ID NO |
|---|---|---|---|---|
| 758 AA [This is the length of the unprocessed precursor] | 78,878 Da [This is the MW of the unprocessed precursor] | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTPHVEITPN VQKEQAHSEE HLGRAAFPGA PGEGPEARGP SLGEDTKEAD LPEPSEKQPA AAPRGKPVSR VPQLKARMVS KSKDGTGSDD KKAKTSTRSS AKTLKNRPCL SPKLPTPGSS DPLIQPSSPA VCPEPPSSPK HVSSVTSRTG SSGAKEMKLK GADGKTKIAT PRGAAPPGQK GQANATRIPA KTPPAPKTPP SSGEPPKSGD RSGYSSPGSP GTPGSRSRTP SLPTPPTREP KKVAVVRTPP KSPSSAKSRL QTAPVPMPDL KNVKSKIGST ENLKHQPGGG KVQIINKKLD LSNVQSKCGS KDNIKHVPGG GSVQIVYKPV DLSKVTSKCG SLGNIHHKPG GGQVEVKSEK LDFKDRVQSK IGSLDNITHV PGGGNKKIET HKLTFRENAK AKTDHGAEIV YKSPVVSGDT SPRHLSNVSS TGSIDMVDSP QLATLADEVS ASLAKQGL | 1-758 | 1 |

Table 2 shows examples of some of the possible multiple sclerosis-associated biomarkers (e.g., Tau protein or a fragment thereof).

1) TABLE 2

| Length (# of Amino Acids) | MW (Daltons) | Amino Acid Sequence | Amino Acids | SEQ ID NO |
|---|---|---|---|---|
| 10 | 1235.4 | MAEPRQEFEV | 1-10 | 2 |
| 20 | 2310.58 | MAEPRQEFEV MEDHAGTYGL | 1-20 | 3 |
| 30 | 3388.69 | MAEPRQEFEV MEDHAGTYGL GDRKDQGGYT | 1-30 | 4 |
| 40 | 4545.84 | MAEPRQEFEV MEDHAGTYGL GDRKDQGGYT MHQDQEGDTD | 1-40 | 5 |
| 50 | 5571.02 | MAEPRQEFEV MEDHAGTYGL GDRKDQGGYT MHQDQEGDTD AGLKESPLQT | 1-50 | 6 |
| 60 | 6570 | MAEPRQEFEV MEDHAGTYGL GDRKDQGGYT MHQDQEGDTD AGLKESPLQT PTEDGSEEPG | 1-60 | 7 |
| 70 | 7574.04 | MAEPRQEFEV MEDHAGTYGL GDRKDQGGYT MHQDQEGDTD AGLKESPLQT PTEDGSEEPG SETSDAKSTP | 1-70 | 8 |
| 80 | 8571.17 | MAEPRQEFEV MEDHAGTYGL GDRKDQGGYT MHQDQEGDTD AGLKESPLQT PTEDGSEEPG SETSDAKSTP TAEDVTAPLV | 1-80 | 9 |
| 90 | 9496.14 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA | 1-90 | 10 |

1)TABLE 2-continued

| Length (# of Amino Acids) | MW (Daltons) | Amino Acid Sequence | Amino Acids | SEQ ID NO |
|---|---|---|---|---|
| 100 | 10556.29 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG | 1-100 | 11 |
| 110 | 11501.26 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD | 1-110 | 12 |
| 120 | 12472.27 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG | 1-120 | 13 |
| 130 | 13565.44 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK | 1-130 | 14 |
| 140 | 14720.77 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP | 1-140 | 15 |
| 150 | 15738.98 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM | 1-150 | 16 |
| 160 | 16660.12 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP | 1-160 | 17 |
| 170 | 17782.35 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP | 1-170 | 18 |
| 180 | 18713.25 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG | 1-180 | 19 |
| 190 | 19822.58 |  | 1-190 | 20 |
| 200 | 20879.8 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMRGAPLLP EGPREATRQP SGTGPEDTEG GRHAPELLKH QLLGDLHQEG | 1-200 | 21 |
| 210 | 21847.88 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE | 1-210 | 22 |

1) TABLE 2-continued

| Length (# of Amino Acids) | MW (Daltons) | Amino Acid Sequence | Amino Acids | SEQ ID NO |
|---|---|---|---|---|
| 220 | 23050.05 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE | 1-220 | 23 |
| 230 | 24062.07 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ | 1-230 | 24 |
| 240 | 25070.18 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA | 1-240 | 25 |
| 250 | 26125.36 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA | 1-250 | 26 |
| 260 | 27062.44 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP | 1-260 | 27 |
| 270 | 28148.74 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD | 1-270 | 28 |
| 280 | 29145.79 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP | 1-280 | 29 |

1) TABLE 2-continued

| Length (# of Amino Acids) | MW (Daltons) | Amino Acid Sequence | Amino Acids | SEQ ID NO |
|---|---|---|---|---|
| 290 | 30141.88 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG | 1-290 | 30 |
| 300 | 31313.22 | MAEPRQEFEV MEDHAGTYGL GDRKDQGGYT MHQDQEGDTD AGLKFSPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP FGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE | 1-300 | 31 |
| 310 | 32422.47 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN | 1-310 | 32 |
| 320 | 33510.63 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKFQAHSEE | 1-320 | 33 |
| 330 | 34449.64 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA | 1-330 | 34 |
| 340 | 35433.69 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP | 1-340 | 35 |

1)TABLE 2-continued

| Length (# of Amino Acids) | MW (Daltons) | Amino Acid Sequence | Amino Acids | SEQ ID NO |
|---|---|---|---|---|
| 350 | 36529.87 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD | 1-350 | 36 |
| 360 | 37535.06 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA | 1-360 | 37 |
| 370 | 38611.37 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR | 1-370 | 38 |
| 380 | 39701.64 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR VPQLKARMVS | 1-380 | 39 |
| 390 | 40719.73 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR VPQLKARMVS KSKDGTGSDD | 1-390 | 40 |
| 400 | 41806.98 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA | 1-400 | 41 |

TABLE 2-continued

| Length (# of Amino Acids) | MW (Daltons) | Amino Acid Sequence | Amino Acids | SEQ ID NO |
|---|---|---|---|---|
| | | QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR VPQLKARMVS KSKDGTGSDD KKAKTSTRSS | | |
| 410 | 42900.36 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR VPQLKARMVS KSKDGTGSDD KKAKTSTRSS AKTLKNRPCL | 1-410 | 42 |
| 420 | 43892.47 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR VPQLKARMVS KSKDGTGSDD KKAKTSTRSS AKTLKNRPCL SPKLPTPGSS | 1-420 | 43 |
| 430 | 44857.59 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR VPQLKARMVS KSKDGTGSDD KKAKTSTRSS AKTLKNRPCL SPKLPTPGSS DPLIQPSSPA | 1-430 | 44 |
| 440 | 45867.71 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR VPQLKARMVS KSKDGTGSDD KKAKTSTRSS AKTLKNRPCL SPKLPTPGSS DPLIQPSSPA VCPEPPSSPK | 1-440 | 45 |
| 450 | 46828.72 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE | 1-450 | 46 |

TABLE 2-continued

| Length (# of Amino Acids) | MW (Daltons) | Amino Acid Sequence | Amino Acids | SEQ ID NO |
|---|---|---|---|---|
| | | RPGSKEEVDE DRDVDESSPQ DSPPSKASPA<br>QDGRPPQTAA REATSIPGFP AEGAIPLPVD<br>FLSKVSTEIP ASEPDGPSVG PAKGQDAPLE<br>FTFHVFITPN VQKEQAHSEE HLGRAAFPGA<br>PGEGPEARGP SLGEDTKEAD LPEPSEKQPA<br>AAPRGKPVSR VPQLKARMVS KSKDGTGSDD<br>KKAKTSTRSS AKTLKNRPCL SPKLPTPGSS<br>DPLIQPSSPA VCPEPPSSPK HVSSVTSRTG | | |
| 460 | 47858.97 | MAEPRQEFEV MEDHAGTYGL GDRKDQGGYT<br>MHQDQEGDTD AGLKESPLQT PTEDGSEEPG<br>SETSDAKSTP TAEDVTAPLV DEGAPGKQAA<br>AQPHTEIPEG TTAEEAGIGD TPSLEDEAAG<br>HVTQEPESGK VVQEGFLREP GPPGLSHQLM<br>SGMPGAPLLP EGPREATRQP SGTGPEDTEG<br>GRHAPELLKH QLLGDLHQEG PPLKGAGGKE<br>RPGSKEEVDE DRDVDESSPQ DSPPSKASPA<br>QDGRPPQTAA REATSIPGFP AEGAIPLPVD<br>FLSKVSTEIP ASEPDGPSVG RAKGQDAPLE<br>FTFHVEITPN VQKEQAHSEE HLGRAAFPGA<br>PGEGPEARGP SLGEDTKEAD LPEPSEKQPA<br>AAPRGKPVSR VPQLKARMVS KSKDGTGSDD<br>KKAKTSTRSS AKTLKNRPCL SPKLPTPGSS<br>DPLIQPSSPA VCPEPPSSPK HVSSVTSRTG<br>SSGAKEMKLK | 1-460 | 47 |
| 470 | 48822.13 | MAEPRQEFEV MEDHAGTYGL GDRKDQGGYT<br>MHQDQEGDTD AGLKESPLQT PTEDGSEEPG<br>SETSDAKSTP TAEDVTAPLV DEGAPGKQAA<br>AQPHTEIPEG TTAEEAGIGD TPSLEDEAAG<br>HVTQSPESGK VVQEGFLREP GPPGLSHQLM<br>SGMPGAPLLP EGPREATRQP SGTGPEDTEG<br>GRHAPELLKH QLLGDLHQEG PPLKGAGGKE<br>RPGSKEEVDE DRDVDSSSPQ DSPPSKASPA<br>QDGRPPQTAA REATSIPGFP AEGAIPLPVD<br>FLSKVSTEIP ASEPDGPSVG RAKDQDAPLE<br>FTFHVEITPN VQKEQAHSEE HLGRAAFPGA<br>PGEGPEARGP SLGEDTKEAD LPEPSEKQPA<br>AAPRGKPVSR VPQLKARMVS KSKDGTGSDD<br>KKAKTSTRSS AKTLKNRPCL SPKLPTPGSS<br>DPLIQPSSPA VCPEPPSSPK HVSSVTSRTG<br>SSGAKEMKLK GADGKTKIAT | 1-470 | 48 |
| 480 | 49775.15 | MAEPRQEFEV MEDHAGTYGL GDRKDQGGYT<br>MHQDQEGDTD AGLKESPLQT PTEDGSEEPG<br>SETSDAKSTP TAEDVTAPLV DEGAPGKQAA<br>AQPHTEIPEG TTAEEAGIGD TPSLEDEAAG<br>HVTQEPESGK VVQEGFLREP GPPGLSHQLM<br>SGMPGAPLLP EGPREATRQP SGTGPEDTEG<br>GRHAPELLKH QLLGDLHQEG PPLKGAGGKE<br>RPGSKEEVDE DRDVDESSPQ DSPPSKASPA<br>QDGRPPQTAA REATSIPGFP AEGAIPLPVD<br>FLSKVSTEIP ASEPDGPSVG RAKGQDAPLE<br>FTFHVEITPN VQKEQAHSEE HLGRAAFPGA<br>PGEGPEARGP SLGEDTKEAD LPEPSEKQPA<br>AAPRGKPVSR VPQLKARMVS KSKDGTGSDD<br>KKAKTSTRSS AKTLKNRPCL SPKLPTPGSS<br>DPLIQPSSPA VCPEPPSSPK HVSSVTSRTG<br>SSGAKEMKLK GADGKTKIAT PRGAAPPGQK | 1-480 | 49 |

TABLE 2-continued

| Length (# of Amino Acids) | MW (Daltons) | Amino Acid Sequence | Amino Acids | SEQ ID NO |
|---|---|---|---|---|
| 490 | 50804.42 | MAEPRQEFEV MEDHAGTYGL GDRKDQGGYT MHQDQEGDTD AGLKESPLQT PTEDGSSEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSSKQPA AAPRGKPVSR VPQLKARMVS KSKDGTGSDD KKAKTSTRSS AKTLKNRPCL SPKLPTPGSS DPLIQPSSPA VCPEPPSSPK HVSSVTSRTG SSGAKEMKLK GADGKTKIAT PRGAAPPGQK GQANATRIPA | 1-490 | 50 |
| 500 | 51782.51 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP APGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR VPQLKARMVS KSKDGTGSDD KKAKTSTRSS AKTLKNRPCL SPKLPTPGSS DPLIQPSSPA VCPEPPSSPK HVSSVTSRTG SSGAKEMKLK GADGKTKIAT PRGAAPPGQK GQANATRIPA KTPPAPKTPP | 1-500 | 51 |
| 410 | 52807.56 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR VPQLKARMVS KSKDGTGSDD KKAKTSTRSS AKTLKNRPCL SPKLPTPGSS DPLIQPSSPA VCPEPPSSPK HVSSVTSRTG SSGAKEMKLK GADGKTKIAT PRGAAPPGQK GQANATRIPA KTPPAPKTPP SSGEPPKSGD | 1-510 | 52 |
| 520 | 53701.53 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKPQAHSEE HLGRAAFPGA PGEGPEARGP SLGEDTKEAD LPEPSGKQPA AAPRGKPVSR VPQLKARMVS KSKDGTGSDD KKAKTSTRSS AKTLKNRPCL SPKLPTPGSS DPLIQPSSPA VCPEPPSSPK HVSSVTSRTG SSGAKEMKLK GADGKTKIAT PRGAAPPGQK GQANATRIPA KTPPAPKTPP SSGEPPKSGD RSGYSSPGSP | 1-520 | 53 |

1) TABLE 2-continued

| Length (# of Amino Acids) | MW (Daltons) | Amino Acid Sequence | | | Amino Acids | SEQ ID NO |
|---|---|---|---|---|---|---|
| 530 | 54735.74 | MAEPRQEFEV MHQDEGDTD SETSDAKSTP AQPHTEIPEG HVTQEPESGK SGMPGAPLLP GRHAPELLKH RPGSKEEVDE QDGRPPQTAA FLSKVSTEIP FTFHVEITPN PGEGPEARGP AAPRGKPVSR KKAKTSTRSS DPLIQPSSPA SSGAKEMKLK GQANATRIPA RSGYSSPGSP | MEDHAGTYGL AGLKESPLQT TAEDVTAPLV TTAEEAGIGD VVQEGFLREP EGPREATRQP QLLGDLHQEG DRDVDESSPQ REATSIPGFP ASEPDGPSVG VQKEQAHSEE SLGEDTKEAD VPQLKARMVS AKTLKNRPCL VCPEPPSSPK GADGKTKIAT KTPPAPKTPP GTPGSRSRTP | GDRKDQGGYT PTEDGSEEPG DEGAPGKQAA TPSLEDEAAG GPPGLSHQLM SGTGPEDTEG PPLKGAGGKE DSPPSKASPA AEGAIPLPVD RAKGQDAPLE HLGRAAFPGA LPEPSEKQPA KSKDGTGSDD SPKLPTPGSS HVSSVTSRTG PRGAAPPGQK SSGEPPKSGD | 1-530 | 54 |
| 540 | 55677.7 | MAEPRQEFEV MHQDEGDTD SETSDAKSTP AQPHTEIPEG HVTQEPESGK SGMPGAPLLP GRHAPELLKH RPGSKEEVDE QDGRPPQTAA FLSKVSTEIP FTFHVEITPN PGEGPEARGP AAPRGKPVSR KKAKTSTRSS DPLIQPSSPA SSGAKEMKLK GQANATRIPA RSGYSSPGSP | MEDHAGTYGL AGLKESPLQT TAEDVTAPLV TTAEEAGIGD VVQEGFLREP EGPREATRQP QLLGDLHQEG DRDVDESSPQ REATSIPGFP ASEPDGPSVG VQKEQAHSEE SLGEDTKEAD VPQLKARMVS AKTLKNRPCL VCPEPPSSPK GADGKTKIAT KTPPAPKTPP GTPGSRSRTP | GDRKDQGGYT PTEDGSEEPG DEGAPGKDAA TPSLEDEAAG GPPGLSHQLM SGTGPEDTEG PPLKGAGGKE DSPPSKASPA AEGAIPLPVD RAKGQDAPLE HLGRAAFPGA LPEPSEKQPA KSKDGTGSDD SPKLPTPGSS HVSSVTSRTG PRGAAPPGQK SSGEPPKSGD SLPTPPTREP | 1-540 | 55 |
| 550 | 56295.63 | MAEPRQEFEV MHQDEGDTD SETSDAKSTP AQPHTEIPEG HVTQEPESGK SGMPGAPLLP GRHAPELLKH RPGSKEEVDE QDGRPPQTAA FLSKVSTEIP FTFHVEITPN PGEGPEARGP AAPRGKPVSR KKAKTSTRSS DPLIQPSSPA SSGAKEMKLK GQANATRIPA RSGYSSPGSP KKVAVVRTPP | MEDHAGTYGL AGLKESPLQT TAEDVTAPLV TTAEDAGIGD VVQEGFLREP EGPREATRQP QLLGDLHQEG DRDVDESSPQ REATSIPGFP ASEPDGPSVG VQKEQAHSEE SLGEDTKEAD VPQLKARMVS AKTLKNRPCL VCPEPPSSPK GADGKTKIAT KTPPAPKTPP GTPGSRSRTP | GDRKDQGGYT PTEDGSEEPG DEGAPGKQAA TPSLEDEAAG GPPGLSHQLM SGTGPEDTEG PPLKGAGGKE DSPPSKASPA ASGAIPLPVD RAKGQDAPLE HLGRAAFPGA LPEPSEKQPA KSKDGTGSDD SPKLPTPGSS HVSSVTSRTG PRGAAPPGQK SSGEPPKSGD SLPTPPTREP | 1-550 | 56 |
| 560 | 57337.84 | MAEPRQEPEV MHQDEGDTD SETSDAKSTP AQPHTEIPEG HVTQEPESGK SGMPGAPLLP GRHAPELLKH RPGSKEEVDE QDGRPPQTAA FLSKVSTEIP FTFHVEITPN PGEGPEARGP | MEDHAGTYGL AGLKESPLQT TAEDVTAPLV TTAEEAGIGD VVQEGFLREP EGPREATRQP QLLGDLHQEG DRDVDESSPQ REATSIPGFP ASEPDGPSVG VQKEQAHSEE SLGEDTKEAD | GDRKDQGGYT PTEDGSEEPG DEGAPGKQAA TPSLEDEAAG GPPGLSHQLM SGTGPEDTEG PPLKGAGGKE DSPPSKESPA AEGAIPLPVD RAKGQDAPLE HLGRAAFPGA LPEPSEKQPA | 1-560 | 57 |

TABLE 2-continued

| Length (# of Amino Acids) | MW (Daltons) | Amino Acid Sequence | Amino Acids | SEQ ID NO |
|---|---|---|---|---|
| | | AAPRGKPVSR VPQLKARMVS KSKDGTGSDD KKAKTSTRSS AKTLKNRPCL SPKLPTPGSS DPLIQPSSPA VCPEPPSSPK HVSSVTSRTG SSGAKEMKLK GADGKTKIAT PRGAAPPGQK GQANATRIPA KTPPAPKTPP SSGEPPKSGD RSGYSSPGSP GTPGSRSRTP SLPTPPTREP KKVAVVRTPP KSPSSAKSRL | | |
| 570 | 58388.1 | MAEPRQEFEV MEDHAGTYGL GDRKDQGGYT MHQDQEGDTD AGLKESPLQT PTEDGSEEPG SETSDAKSTP TAEDVTAPLV DPGAPKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR VPQLKARMVS KSKDGTGSDD KKAKTSTRSS AKTLKNRPCL SPKLPTPGSS DPLIQPSSPA VCPEPPSSPK HVSSVTSRTG SSGAKEMKLK GADGKTKIAT PRGAAPPGQK GQANATRIPA KTPPAPKTPP SSGEPPKSGD RSGYSSPGSP GTPGSRSRTP SLPTPPTREP KKVAVVRTPP KSPSSAKSRL QTAPVPMPDL | 1-570 | 58 |
| 580 | 59431.32 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG AVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLP FTFHVEITPN VQKEQAHSEE HLGRAAFPGA PGEGPEARGP SLGEDTKEAD LPEPSEKQPA AAPRGKPVSR VPQLKARMVS KSKDGTGSDD KKAKTSTRSS AKTLKNRPCL SPKLPTPGSS DPLIQPSSPA VCPEPPSSPK HVSSVTSRTG SSGAKEMKLK GADGKTKIAT PRGAAPPGQK GQANATRIPA KTPPAPKTPP SSGEPPKSGD RSGYSSPGSP GTPGSRSRTP SLPTPPTREP KKVAVVRTPP KSPSSAKSRL QTAPVPMPDL KNVKSKIGST | 1-580 | 59 |
| 590 | 60449.41 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR VPQLKARMVS KSKDGTGSDD KKAKTSTRSS AKTLKNRPCL SPKLPTPGSS DPLIQPSSPA VCPEPPSSPK HVSSVTSRTG SSGAKEMKLK GADGKTKIAT PRGAAPPGQK GQANATRIPA KTPPAPKTPP SSGEPPKSGD RSGYSSPGSP GTPGSRSRTP SLPTPPTREP KKVAVVRTPP KSPSSAKSRL QTAPVPMPDL KNVKSKIGST ENLKHQPGGG | 1-590 | 60 |
| 600 | 61629.85 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG | 1-600 | 61 |

TABLE 2-continued

| Length (# of Amino Acids) | MW (Daltons) | Amino Acid Sequence | Amino Acids | SEQ ID NO |
|---|---|---|---|---|
| | | GRHAPELLKH QLLGDLHQEG PPLKGAGGKE<br>RPGSKEEVDE DRDVDESSPQ DSPPSKASPA<br>QDGRPPQTAA REATSIPGFP AEGAIPLPVD<br>FLSKVSTEIP ASEPDGPSVG RAKGQDAPLE<br>FTFHVEITPN VQKEQAHSEE HLGRAAFPGA<br>PGEGPEARGP SLGEDTKEAD LPEPSEKQPA<br>AAPRGKPVSR VPQLKARMVS KSKDGTGSDD<br>KKAKTSTRSS AKTLKNRPCL SPKLPTPGSS<br>DPLIQPSSPA VCPEPPSSPK HVSSVTSRTG<br>SSGAKEMKLK GADGKTKIAT PRGAAPPGQK<br>GQANATRIPA KTPPAPKTPP SSGEPPKSGD<br>RSGYSSPGSP GTPGSRSRTP SLPTPPTREP<br>KKVAVVRTPP KSPSSAKSRL QTAPVPMPDL<br>KNVKSKIGST ENLKHQPGGG KVQIINKKLD | | |
| 610 | 62633.98 | MAEPRQEFEV MEDHAGTYGL GDRKDQGGYT<br>MHQDQEGDTD AGLKESPLQT PTEDGSEEPG<br>SETSDAKSTP TAEDVTAPLV DEGAPGKQAA<br>AQPHTEIPEG TTAEEAGIGD TPSLEDEAAG<br>HVTQEPESGK VVQEGFLREP GPPGLSHQLM<br>SGMPGAPLLP EGPREATRQP SGTGPEDTEG<br>GRHAPELLKH QLLGDLHQEG PPLKGAGGKE<br>RPGSKEEVDE DRDVDESSPQ DSPPSKASPA<br>QDGRPPQTAA REATSIPGFP AEGAIPLPVD<br>FLSKVSTEIP ASEPDGPSVG RAKGQDAPLE<br>FTFHVEITPN VQKEQAHSEE HLGRAAFPGA<br>PGEGPEARGP SLGEDTKEAD LPEPSEKQPA<br>AAPRGKPVSR VPQLKARMVS KSKDGTGSDD<br>KKAKTSTRSS AKTLKNRPCL SPKLPTPGSS<br>DPLIQPSSPA VCPEPPSSPK HVSSVTSRTG<br>SSGAKEMKLK GADGKTKIAT PRGAAPPGQK<br>GQANATRIPA KTPPAPKTPP SSGEPPKSGD<br>RSGYSSPGSP GTPGSRSRTP SLPTPPTREP<br>KKVAVVRTPP KSPSSAKSRL QTAPVPMPDL<br>KNVKSKIGST ENLKHQPGGG KVQIINKKLD<br>LSNVQSKCGS | 1-610 | 62 |
| 620 | 63680.16 | MAEPRQEFEV MEDHAGTYGL GDRKDQGGYT<br>MHQDQEGDTD AGLKESPLQT PTEDGSEEPG<br>SETSDAKSTP TAEDVTAPLV DEGAPGKQAA<br>AQPHTEIPEG TTAEEAGIGD TPSLEDEAAG<br>HVTQEPESGK VVQEGFLREP GPPGLSHQLM<br>SGMPGAPLLP EGPREATRQP SGTGPEDTEG<br>GRHAPELLKH QLLGDLHQEG PPLKGAGGKE<br>RPGSKEEVDE DRDVDESSPQ DSPPSKASPA<br>QDGRPPQTAA REATSIPGFP AEGAIPLPVD<br>FLSKVSTEIP ASEPDGPSVG RAKGQDAPLE<br>FTFHVEITPN VQKEQAHSEE HLGRAAFPGA<br>PGEGPEARGP SLGEDTKEAD LPEPSEKQPA<br>AAPRGKPVSR VPQLKARMVS KSKDGTGSDD<br>KKAKTSTRSS AKTLKNRPCL SPKLPTPGSS<br>DPLIQPSSPA VCPEPPSSPK HVSSVTSRTG<br>SSGAKEMKLK GADGKTKIAT PRGAAPPGQK<br>GQANATRIPA KTPPAPKTPP SSGEPPKSGD<br>RSGYSSPGSP GTPGSRSRTP SLPTPPTREP<br>KKVAVVRTPP KSPSSAKSRL QTAPVPMPDL<br>KNVKSKIGST ENLKHQPGGG KVQIINKKLD<br>LSNVQSKCGS KDNIKHVPGG | 1-620 | 63 |
| 630 | 64751.44 | MAEPRQEFEV MEDHAGTYGL GDRKDQGGYT<br>MHQDQEGDTD AGLKESPLQT PTEDGSEEPG<br>SETSDAKSTP TAEDVTAPLV DEGAPGKQAA<br>AQPHTEIPEG TTAEEAGIGD TPSLEDEAAG<br>HVTQEPESGK VVQEGFLREP GPPGLSHQLM<br>SGMPGAPLLP EGPREATRQP SGTGPEDTEG<br>GRHAPELLKH QLLGDLHQEG PPLKGAGGKE<br>RPGSKEEVDE DRDVDESSPQ DSPPSKASPA<br>QDGRPPQTAA REATSIPGFP AEGAIPLPVD<br>FLSKVSTEIP ASEPDGPSVG RAKGQDAPLE<br>FTFHVEITPN VQKEQAHSEE HLGRAAFPGA<br>PGEGPEARGP SLGEDTKEAD LPEPSEKQPA<br>AAPRGKPVSR VPQLKARMVS KSKDGTGSDD<br>KKAKTSTRSS AKTLKNRPCL SPKLPTPGSS<br>DPLIQPSSPA VCPEPPSSPK HVSSVTSRTG<br>SSGAKEMKLK GADGKTKIAT PRGAAPPGQK<br>GQANATRIPA KTPPAPKTPP SSGEPPKSGD | 1-630 | 64 |

1) TABLE 2-continued

| Length (# of Amino Acids) | MW (Daltons) | Amino Acid Sequence | | Amino Acids | SEQ ID NO |
|---|---|---|---|---|---|
| | | RSGYSSPGSP | GTPGSRSRTP SLPTPPTREP | | |
| | | KKVAVVRTPP | KSPSSAKSRL QTAPVPMPDL | | |
| | | KNVKSKIGST | ENLKHQPGGG KVQIINKKLD | | |
| | | LSNVQSKCGS | KDNIKHVPGG GSVQIVYKPV | | |
| 640 | 65770.63 | MAEPRQEFEV | MEDHAGTYGL GDRKDQGGYT | 1-640 | 65 |
| | | MHQDQEGDTD | AGLKESPLQT PTEDGSEEPG | | |
| | | SETSDAKSTP | TAEDVTAPLV DEGAPGKQAA | | |
| | | AQPHTEIPEG | TTAEEAGIGD TPSLEDEAAG | | |
| | | HVTQEPESGK | VVQEGFLREP GPPGLSHQLM | | |
| | | SGMPGAPLLP | EGPREATRQP SGTGPEDTEG | | |
| | | GRHAPELLKH | QLLGDLHQEG PPLKGAGGKE | | |
| | | RPGSKEEVDE | DRDVDESSPQ DSPPSKASPA | | |
| | | QDGRPPQTAA | REATSIPGFP AEGAIPLPVD | | |
| | | FLSKVSTEIP | ASEPDGPSVG RAKGQDAPLE | | |
| | | FTFHVEITPN | VQKEQAHSEE HLGRAAFPGA | | |
| | | PGEGPEARGP | SLGEDTKEAD LPEPSEKQPA | | |
| | | AAPRGKPVSR | VPQLKARMVS KSKDGTGSDD | | |
| | | KKAKTSTRSS | AKTLKNRPCL SPKLPTPGSS | | |
| | | DPLIQPSSPA | VCPEPPSSPK HVSSVTSRTG | | |
| | | SSGAKEMKLK | GADGKTKIAT PRGAAPPGQK | | |
| | | GQANATRIPA | KTPPAPKTPP SSGEPPKSGD | | |
| | | RSGYSSPGSP | GTPGSRSRTP SLPTPPTREP | | |
| | | KKVAVVRTPP | KSPSSAKSRL QTAPVPMPDL | | |
| | | KNVKSKIGST | FNLKHQPGGG KVQIINKKLD | | |
| | | LSNVQSKCGS | KDNIKHVPGG GSVQIVYKPV | | |
| | | DLSKVTSKCG | | | |
| 650 | 66811.8 | MAEPRQEFEV | MEDHAGTYGL GDRKDQGGYT | 1-650 | 66 |
| | | MHQDQEGDTD | AGLKESPLQT PTEDGSEEPG | | |
| | | SETSDAKSTP | TAEDVTAPLV DEGAPGKQAA | | |
| | | AQPHTEIPEG | TTAEEAGIGD TPSLEDEAAG | | |
| | | HVTQEPESGK | VVQEGFLREP GPPGLSHQLM | | |
| | | SGMPGAPLLP | EGPREATRQP SGTGPEDTEG | | |
| | | GRHAPELLKH | QLLGDLHQEG PPLKGAGGKE | | |
| | | RPGSKEEVDE | DRDVDESSPQ DSPPSKASPA | | |
| | | QDGRPPQTAA | REATSIPGFP AEGAIPLPVD | | |
| | | FLSKVSTEIP | ASEPDGPSVG RAKGQDAPLE | | |
| | | FTFHVEITPN | VQKEQAHSEE HLGRAAFPGA | | |
| | | PGEGPEARGP | SLGEDTKEAD LPEPSEKQPA | | |
| | | AAPRGKPVSR | VPQLKARMVS KSKDGTGSDD | | |
| | | KKAKTSTRSS | AKTLKNRPCL SPKLPTPGSS | | |
| | | DPLIQPSSPA | VCPEPPSSPK HVSSVTSRTG | | |
| | | SSGAKEMKLK | GADGKTKIAT PRGAAPPGQK | | |
| | | GQANATRIPA | KTPPAPKTPP SSGEPPKSGD | | |
| | | RSGYSSPGSP | GTPGSRSRTP SLPTPPTREP | | |
| | | KKVAVVRTPP | KSPSSAKSRL QTAPVPMPDL | | |
| | | KNVKSKIGST | ENLKHQPGGG KVQIINKKLD | | |
| | | LSNVQSKCGS | KDNIKHVPGG GSVQIVYKPV | | |
| | | DLSKVTSKCG | SLGNIHHKPG | | |
| 660 | 67853.95 | MAEPRQEFEV | MEDHAGTYGL GDRKDQGGYT | 1-660 | 67 |
| | | MHQDQEGDTD | AGLKESPLQT PTEDGSEEPG | | |
| | | SETSDAKSTP | TAEDVTAPLV DEGAPGKQAA | | |
| | | AQPHTEIPEG | TTAEEAGIGD TPSLEDEAAG | | |
| | | HVTQEPESGK | VVQEGFLREP GPPGLSHQLM | | |
| | | SGMPGAPLLP | EGPREATRQP SGTGPEDTEG | | |
| | | GRHAPELLKH | QLLGDLHQEG PPLKGAGGKE | | |
| | | RPGSKEEVDE | DRDVDESSPQ DSPPSKASPA | | |
| | | QDGRPPQTAA | REATSIPGFP AEGAIPLPVD | | |
| | | FLSKVSTEIP | ASEPDGPSVG RAKGQDAPLE | | |
| | | FTFHVEITPN | VQKEQAHSEE HLGRAAFPGA | | |
| | | PGEGPEARGP | SLGEDTKEAD LPEPSEKQPA | | |
| | | AAPRGKPVSR | VPQLKARMVS KSKDGTGSDD | | |
| | | KKAKTSTRSS | AKTLKNRPCL SPKLPTRGSS | | |
| | | DPLIQPSSPA | VCPEPPSSPK HVSSVTSRTG | | |
| | | SSGAKEMKLK | GADGKTKIAT PRGAAPPGQK | | |
| | | GQANATRIPA | KTPPAPKTPP SSGEPPKSGD | | |
| | | RSGYSSPGSP | GTPGSRSRTP SLPTPPTREP | | |
| | | KKVAVVRTPP | KSPSSAKSRL QTAPVPMPDL | | |
| | | KNVKSKIGST | ENLKHQPGGG KVQIINKKLD | | |
| | | LSNVQSKCGS | KDNIKHVPGG GSVQIVYKPV | | |
| | | DLSKVTSKCG | SLGNIHHKPG GGQVEVKSEK | | |

1) TABLE 2-continued

| Length (# of Amino Acids) | MW (Daltons) | Amino Acid Sequence | Amino Acids | SEQ ID NO |
| --- | --- | --- | --- | --- |
| 670 | 69071.34 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR VPQLKARMVS KSKDGTGSDD KKAKTSTRSS AKTLKNRPCL SPKLPTPGSS DPLIQPSSPA VCPEPPSSPK HVSSVTSRTG SSGAKEMKLK GADGKTKIAT PRGAAPPGQK GQANATRIPA KTPPAPKTPP SSGEPPKSGD RSGYSSPGSP GTPGSRSRTP SLPTPPTREP KKVAVVRTPP KSPSSAKSRL QTAPVPMPDL KNVKSKIGST ENLKHQPGGG KVQIINKKLD LSNVQSKCGS KDNIKHVPGG GSVQIVYKPV DLSKVTSKCG SLGNIHHKPG GGQVEVKSEK LDFKDRVQSK | 1-670 | 68 |
| 680 | 70121.52 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGKGPEARGP SLGEDTKEAD LPEPSEKQPA AAPRGKPVSR VPQLKARMVS KSKDGTGSDD KKAKTSTRSS AKTLKNRPCL SPKLPTPGSS DPLIQPSSPA VCPEPPSSPK HVSSVTSRTG SSGAKEMKLK GADGKTKIAT PRGAAPPGQK GQANATRIPA KTPPAPKTPP SSGEPPKSGD RSGYSSPGSP GTPGSRSRTP SLPTPPTREP KKVAVVRTPP KSPSSAKSRL QTAPVPMPDL KNVKSKIGST ENLKHQPGGG KVQIINKKLD LSNVQSKCGS KDNIKHVPGG GSVQIVYKPV DLSKVTSKCG SLGNIHHKPG GGQVEVKSEK LDFKDRVQSK IGSLDNITHV | 1-680 | 69 |
| 690 | 71103.62 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR VPQLKARMVS KSKDGTGSDD KKAKTSTRSS AKTLKNRPCL SPKLPTPGSS DPLIQPSSPA VCPEPPSSPK HVSSVTSRTG SSGAKEMKLK GADGKTKIAT PRGAAPPGQK GQANATRIPA KTPPAPKTPP SSGEPPKSGD RSGYSSPGSP GTPGSRSRTP SLPTPPTREP KKVAVVRTPP KSPSSAKSRL QTAPVPMPDL KNVKSKIGST ENLKHQPGGG KVQIINKKLD LSNVQSKCGS KDNIKHVPGG GSVQIVYKPV DLSKVTSKCG SLGNIHHKPG GGQVEVKSEK LDFKDRVQSK IGSLDNITHV PGGGNKKIET | 1-690 | 70 |

TABLE 2-continued

| Length (# of Amino Acids) | MW (Daltons) | Amino Acid Sequence | Amino Acids | SEQ ID NO |
|---|---|---|---|---|
| 700 | 72329.04 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR VPQLKARMVS KSKDGTGSDD KKAKTSTRSS AKTLKNRPCL SPKLPTPGSS DPLIQPSSPA VCPEPPSSPK HVSSVTSRTG SSGAKEMKLK GADGKTKIAT PRGAAPPGQK GQANATRIPA KTPPAPKTPP SSGEPPKSGD RSGYSSPGSP GTPGSRSRTP SLPTPPTREP KKVAVVRTPP KSPSSAKSRL QTAPVPMPDL KNVKSKIGST ENLKHQPGGG KVQIINKKLD LSNVQSKCGS KDNIKHVPGG GSVQIVYKPV DLSKVTSKCG SLGNIHHKPG GGQVEVKSEK LDFKDRVQSK IGSLDNITHV PGGGNKKIET HKLTFRENAK | 1-700 | 71 |
| 710 | 73351.17 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR VPQLKARMVS KSKDGTGSDD KKAKTSTRSS AKTLKNRPCL SPKLPTPGSS DPLIQPSSPA VCPEPPSSPK HVSSVTSRTG SSGAKEMKLK GADGKTKIAT PRGAAPPGQK GQANATRIPA KTPPAPKTPP SSGEPPKSGD RSGYSSPGSP GTPGSRSRTP SLPTPPTREP KKVAVVRTPP KSPSSAKSRL QTAPVPMPDL KNVKSKIGST ENLKHQPGGG KVQIINKKLD LSNVQSKCGS KDNIKHVPGG GSVQIVYKPV DLSKVTSKCG SLGNIHHKPG GGQVEVKSEK LDFKDRVQSK IGSLDNITHV PGGGNKKIET HKLTFRENAK AKTDHGAEIV | 1-710 | 72 |
| 720 | 74385.31 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR VPQLKARMVS KSKDGTGSDD KKAKTSTRSS AKTLKNRPCL SPKLPTPGSS DPLIQPSSPA VCPEPPSSPK HVSSVTSRTG SSGAKEMKLK GADGKTKIAT PRGAAPPGQK GQANATRIPA KTPPAPKTPP SSGEPPKSGD RSGYSSPGSP GTPGSRSRTP SLPTPPTREP KKVAVVRTPP KSPSSAKSRL QTAPVPMPDL KNVKSKIGST ENLKHQPGGG KVQIINKKLD LSNVQSKCGS KDNIKHVPGG GSVQIVYKPV DLSKVTSKCG SLGNIHHKPG GGQVEVKSEK LDFKDRVQSK IGSLDNITHV PGGGNKKIET HKLTFRENAK AKTDHGAEIV YKSPVVSGDT | 1-720 | 73 |

1)TABLE 2-continued

| Length (# of Amino Acids) | MW (Daltons) | Amino Acid Sequence | Amino Acids | SEQ ID NO |
|---|---|---|---|---|
| 730 | 75450.47 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR VPQLKARMVS KSKDGTGSDD KKAKTSTRSS AKTLKNRPCL SPKLPTPGSS DPLIQPSSPA VCPEPPSSPK HVSSVTSRTG SSGAKEMKLK GADGKTKIAT PRGAAPPGQK GQANATRIPA KTPPAPKTPP SSGEPPKSGD RSGYSSPGSP GTPGSRSRTP SLPTPPTREP KKVAVVRTPP KSPSSAKSRL QTAPVPMPDL KNVKSKIGST ENLKHQPGGG KVQIINKKLD LSNVQSKCGS KDNIKHVPGG GSVQIVYKPV DLSKVTSKCG SLGNIHHKPG GGQVEVKSEK LDFKDRVQSK IGSLDNITHV PGGGNKKIET HKLTFRENAK AKTDHGAEIV YKSPVVSGDT SPRHLSNVSS | 1-730 | 74 |
| 740 | 76804.91 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP EGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR VPQLKARMVS KSKDGTGSDD KKAKTSTRSS AKTLKNRPCL SPKLPTPGSS DPLIQPSSPA VCPEPPSSPK HVSSVTSRTG SSGAKEMKLK GADGKTKIAT PRGAAPPGQK GQANATRIPA KTPPAPKTPP SSGEPPKSGD RSGYSSPGSP GTPGSRSRTP SLPTPPTREP KKVAVVRTPP KSPSSAKSRL QTAPVPMPDL KNVKSKIGST ENLKHQPGGG KVQIINKKLD LSNVQSKCGS KDNIKHVPGG GSVQIVYKPV DLSKVTSKCG SLGNIHHKPG GGQVEVKSEK LDFKDRVQSK IGSLDNITHV PGGGNKKIET HKLTFRENAK AKTDHGAEIV YKSPVVSGDT SPRHLSNVSS TGSIDMVDSP | 1-740 | 75 |
| 750 | 78109.39 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQEPESGK VVQEGFLREP GPPGLSHQLM SGMPGAPLLP SGPREATRQP SGTGPEDTEG GRHAPELLKH QLLGDLHQEG PPLKGAGGKE RPGSKEEVDE DRDVDESSPQ DSPPSKASPA QDGRPPQTAA REATSIPGFP AEGAIPLPVD FLSKVSTEIP ASEPDGPSVG RAKGQDAPLE FTFHVEITPN VQKEQAHSEE HLGRAAFPGA PGEGPEARGP SLGEDTKEAD LPEPSEKQPA AAPRGKPVSR VPQLKARMVS KSKDGTGSDD KKAKTSTRSS AKTLKNRPCL SPKLPTPGSS DPLIQPSSPA VCPEPPSSPK HVSSVTSRTG SSGAKEMKLK GADGKTKIAT PRGAAPPGQK GQANATRIPA KTPPAPKTPP SSGEPPKSGD RSGYSSPGSP GTPGSRSRTP SLPTPPTREP | 1-750 | 76 |

1) TABLE 2-continued

| Length (# of Amino Acids) | MW (Daltons) | Amino Acid Sequence | Amino Acids | SEQ ID NO |
|---|---|---|---|---|
| | | KKVAVVRTPP KSPSSAKSRL QTAPVPMPDL KNVKSKIGST ENLKHQPGGG KVQIINKKLD LSNVQSKCGS KDNIKHVPGG GSVQIVYKPV DLSKVTSKCG SLGNIHHKPG GGQVEVKSEK LDFKDRVQSK IGSLDNITHV PGGGNKKIET HKLTFRENAK AKTDHGAEIV YKSPVVSGDT SPRHLSNVSS TGSIDMVDSP QLATLADEVS | | |
| 10 | 1815.06 | QLATLADEVS ASLAKQGL | 749-758 | 77 |
| 20 | 2818.17 | TGSIDMVDSP QLATLADEVS ASLAKQGL | 739-758 | 78 |
| 30 | 2992.33 | SS TGSIDMVDSP QLATLADEVS ASLAKQGL | 729-758 | 79 |
| 40 | 4099.53 | DT SPRHLSNVSS TGSIDMVDSP QLATLADEVS ASLAKQGL | 719-758 | 80 |

In some embodiments, the step of detecting the multiple sclerosis-associated biomarker in the sample may comprise introducing an antibody to the sample, wherein the antibody binds to the multiple sclerosis-associated biomarker.

In some embodiments, the step of detecting the multiple sclerosis-associated biomarker in the sample comprises subjecting the sample to a western blot, an enzyme-linked immunosorbent assay (ELISA), a lateral flow assay, a radioimmunoassay, an immunohistochemistry assay, a bioluminescent assay, a chemiluminescent assay, a mass spectrometry assay, a flow cytometry assay (e.g., florescence-activated cell sorting (FACS)), or a combination thereof and the like. Such assays are well known in the art.

In some embodiments, the step of detecting the multiple sclerosis-associated biomarker further comprises contacting the sample with an antibody that binds to the multiple sclerosis-associated biomarker and detecting an antibody-biomarker complex. The step of detecting an antibody-biomarker complex may comprise subjecting the sample to a micro array, western blot, an enzyme-linked immunosorbent assay (ELISA), a lateral flow assay, a radioimmunoassay, an immunohistochemistry assay, a bioluminescent assay, a chemiluminescent assay, a flow cytometry assay (e.g., florescence-activated cell sorting (FACS)), or a combination thereof and the like. In some embodiments, detecting the antibody-biomarker complex indicates the presence of multiple sclerosis or a risk of multiple sclerosis.

As described above, in some embodiments, the step of detecting the multiple sclerosis-associated biomarker may comprise subjecting the sample florescence-activated cell sorting (FACS). Fluorescence-activated cell sorting (FACS) is a type of flow cytometry that sorts a mixture of biological cells, one at a time, into separate containers based upon the specific light scattering and fluorescent characteristics of each cell. It provides quantitative recording of fluorescent signals from individual cells as well as physical separation of cells of particular interest. Generally, a current of a rapidly flowing stream of liquid carries a suspension of cells through a nozzle. The flow is selected such that there is a large separation between cells relative to their diameter. Vibrations at the tip of the nozzle cause the stream of cells to break into individual droplets, and the system is adjusted so that there is a low probability of more than one cell being in a droplet. A monochromatic laser beam illuminates the droplets, which are electronically monitored by fluorescent detectors. The droplets that emit the proper fluorescent wavelengths are electrically charged between deflection plates in order to be sorted into collection tubes.

As described above, in some embodiments, the step of detecting the multiple sclerosis-associated biomarker may comprise subjecting the sample to an enzyme-linked immunosorbent assay (ELISA). ELISA is an assay used to detect the presence of an antibody or a biomarker in a sample. Generally, in ELISA, a sample containing an unknown amount of biomarker, e.g., an antigen, is affixed/immobilized to a surface (e.g., a polystyrene microtiter plate). Then, an antibody that binds to the antigen of interest is washed over the surface so that it can bind the antigen and form an antibody/antigen complex. In some cases, this antibody is covalently linked to an enzyme. In some cases, the antibody is not covalently linked to an enzyme but can be detected by a secondary antibody that is linked to an enzyme. In the final step, a substance (e.g., substrate) that the enzyme is capable of converting to a detectable visible signal (e.g., color signal) is added to the reaction. Thus, if the antibody/antigen complex is present, the substrate will be converted to the detectable visible signal, and then amount of antigen in the sample can be measured.

As mentioned above, in some embodiments, an antibody is used to detect the presence of the multiple sclerosis-associated biomarker. The multiple sclerosis-associated biomarker may be detected with a variety of antibodies. In some embodiments, the antibody is a monoclonal or a polyclonal antibody. In some embodiments, the antibody is a humanized antibody. In some embodiments, the antibody is a chimera. In some embodiments, the antibody is derived from a human, a mouse, a rat, a llama, a rabbit, a dog, a primate, a guinea pig, a cat, a hamster, a pig, a chicken, a goat, a horse, or a cow. In some embodiments, the antibody is synthetic. In some embodiments, the antibody is a recombinant antibody.

Frequently, antibodies are labelled either covalently or non-covalently by combining the antibody with a second substance that provides for detectable signal. A wide variety of labels and conjugation techniques are known in the art and are reported extensively in both the scientific and patent literature. Examples of labels include but are not limited to radioisotopes, enzymes, substrates, cofactors, inhibitors, fluorescers, chemiluminescers, magnetic particles, and the like. In some embodiments of the present invention, the antibody comprises a label.

In some embodiments, the present invention is used to detect the presence of multiple sclerosis. For example, a patient may present with symptoms of a demyelinating disease, and he or she is tested for an elevated level of a multiple sclerosis-associated biomarker. If, according to the present invention, the level of a multiple sclerosis-associated biomarker is elevated and the patient presents symptoms of a demyelinating disease, then the patient is diagnosed as having multiple sclerosis.

In some embodiments, the present invention is used to detect a risk of multiple sclerosis. For example, a patient may present with no symptoms of a demyelinating disease, but he or she wishes to be tested for a risk of multiple sclerosis. If, according to the present invention, the level of a multiple sclerosis-associated biomarker is elevated and the patient does not present symptoms of a demyelinating disease, then the patient is diagnosed as having a risk of multiple sclerosis.

As used herein, the term "elevated level" refers to a level that is higher than the normal level of the multiple sclerosis-associated biomarker (e.g., the level that would be detected in a person who does not have multiple sclerosis). To identify the level of the multiple sclerosis-associated biomarker that is the normal level, samples are pooled from about, for example, 500 patients (or an appropriate number of patients that would be statistically meaningful) who do not experience any symptoms of multiple sclerosis (or other demyelinating diseases) and who do not test positive for multiple sclerosis as detected by MRI. From those pooled samples, the average level of the multiple sclerosis-associated biomarker can be quantified and then defined as being the normal level of the multiple sclerosis-associated biomarker. If the normal level of the multiple sclerosis-associated biomarker is about zero, then an elevated level refers to any level that is greater than zero, for example, about 5 units, about 25 units, about 50 units, about 100 units, about 500 units, about 1000 units, about 10,000 units, about 100,000 units, about 1,000,000 units. In some embodiments, a unit may be an absorbance unit (e.g., from an ELISA), a percent positive (e.g., from a flow cytometry or FACS assay), or a fluorescence unit.

If the normal level of the multiple sclerosis-associated biomarker is some positive value (e.g., 5 units, 10 units, 50 units, 100 units, 500 units), then an elevated level refers to any level that is higher than the normal level. In some embodiments, an elevated level of the multiple sclerosis-associated biomarker may be a level that is about 10-20% higher than the normal level of the multiple sclerosis-associated biomarker. In some embodiments, an elevated level of the multiple sclerosis-associated biomarker may be a level that is about 20-30% higher than the normal level of the multiple sclerosis-associated biomarker. In some embodiments, an elevated level of the multiple sclerosis-associated biomarker may be a level that is about 30-40% higher than the normal level of the multiple sclerosis-associated biomarker. In some embodiments, an elevated level of the multiple sclerosis-associated biomarker may be a level that is about 40-50% higher than the normal level of the multiple sclerosis-associated biomarker. In some embodiments, an elevated level of the multiple sclerosis-associated biomarker may be a level that is about 50-60% higher than the normal level of the multiple sclerosis-associated biomarker. In some embodiments, an elevated level of the multiple sclerosis-associated biomarker may be a level that is about 60-70% higher than the normal level of the multiple sclerosis-associated biomarker. In some embodiments, an elevated level of the multiple sclerosis-associated biomarker may be a level that is about 70-80% higher than the normal level of the multiple sclerosis-associated biomarker. In some embodiments, an elevated level of the multiple sclerosis-associated biomarker may be a level that is about 80-90% higher than the normal level of the multiple sclerosis-associated biomarker. In some embodiments, an elevated level of the multiple sclerosis-associated biomarker may be a level that is about 90-100% higher than the normal level of the multiple sclerosis-associated biomarker. In some embodiments, an elevated level of the multiple sclerosis-associated biomarker may be a level that is about 1-2 fold higher than the normal level of the multiple sclerosis-associated biomarker. In some embodiments, an elevated level of the multiple sclerosis-associated biomarker may be a level that is about 2-3 fold higher than the normal level of the multiple sclerosis-associated biomarker. In some embodiments, an elevated level of the multiple sclerosis-associated biomarker may be a level that is about 3-4 fold higher than the normal level of the multiple sclerosis-associated biomarker. In some embodiments, an elevated level of the multiple sclerosis-associated biomarker may be a level that is about 4-5 fold higher than the normal level of the multiple sclerosis-associated biomarker. In some embodiments, an elevated level of the multiple sclerosis-associated biomarker may be a level that is about 5-10 fold higher than the normal level of the multiple sclerosis-associated biomarker. In some embodiments, an elevated level of the multiple sclerosis-associated biomarker may be a level that is about 10-20 fold higher than the normal level of the multiple sclerosis-associated biomarker. In some embodiments, an elevated level of the multiple sclerosis-associated biomarker may be a level that is about 20-50 fold higher than the normal level of the multiple sclerosis-associated biomarker.

The present invention also provides a method of monitoring the progression of multiple sclerosis and/or monitoring the treatment of multiple sclerosis. For example, in some embodiments, the present invention may be used to measure the level of the multiple sclerosis-associated biomarker in order to detect a change in the level (e.g., an increase in the level, a decrease in the level, a maintaining of the level). Without wishing to limit the present invention to any theory or mechanism, a change in the level of the multiple sclerosis-associated biomarker may correlate with a change in the patient's status (e.g., remission, progression, worsening). For example, a decrease in the level of the multiple sclerosis-associated biomarker may indicate the patient has entered or will enter a remission period. In some embodiments, the present invention may be used to monitor the level of the multiple sclerosis-associated biomarker in a patient while the patient is on a treatment regimen (e.g., a drug). Without wishing to limit the present invention to any theory or mechanism, a treatment regimen (e.g., a drug) that is effective at inhibiting the progression of multiple sclerosis and/or reducing the symptoms of multiple sclerosis may decrease the level of the multiple sclerosis-associated biomarker in the patient.

As mentioned above, in some embodiments, the method of the present invention for detecting multiple sclerosis is used in combination with one or more different methods for detecting multiple sclerosis. For example, in some cases, a combination of family history, a physical exam, and magnetic resonance imaging (MRI) findings are used to diagnose multiple sclerosis. Currently, MRI is the most sensitive radiographic technique for the imaging of multiple sclerosis. Multiple sclerosis plaques are commonly seen as round or void discrete lesions in the periventricular white matter. Other common locations for multiple sclerosis plaques include the corpus callosum, corona radiate, internal capsule, and centrum semiovale. In some embodiments, the present invention is used to measure a multiple sclerosis-associated biomarker, and the level of the multiple sclerosis-associated biomarker is correlated with a magnetic resonance imaging (MRI) measurement. Without wishing to limit the present invention to any theory or mechanism, it is believed that elevated levels of the multiple sclerosis-associated biomarker correlate with a MRI scan showing the presence of multiple sclerosis plaques in the brain.

The method of the present invention for detecting multiple sclerosis may be used in combination with one or more methods for detecting a different condition. For example, the method of the present invention may also help to distinguish multiple sclerosis from other diseases with similar clinical manifestations. For example, neuromyelitis optica (NMO), also known as Devic's syndrome, is a neurological disorder regarded as a severe variant of multiple sclerosis. The characteristic inflammatory demyelinating lesions of NMO selectively and repeatedly affect the optic nerves and the spinal cord, causing blindness and paralysis. A marker (e.g., aquaporin-4 antibodies) has been identified in serum and cerebrospinal fluid of patients with NMO, and the presence of a NMO marker (e.g., aquaporin-4 antibodies) may be used to distinguish NMO from multiple sclerosis. In some embodiments, the method of detecting the presence of multiple sclerosis or a risk of multiple sclerosis comprises detecting the presence or absence of at least two biomarkers (e.g., proteins, antigens, or the like) wherein at least one biomarker is detected in order to distinguish multiple sclerosis from a disease with similar clinical manifestations.

In some embodiments, the method of detecting the presence of multiple sclerosis or a risk of multiple sclerosis comprises detecting an elevated level of two or more multiple sclerosis-associated biomarkers. In some embodiments, the method of detecting the presence of multiple sclerosis or a risk of multiple sclerosis comprises detecting an elevated level of three or more multiple sclerosis-associated biomarkers.

The present invention also provides a method of diagnosing multiple sclerosis at an early stage of the disease before all clinical criteria are fulfilled thus justifying early initiation of a multiple sclerosis-appropriate therapy.

A Kit for Detecting the Presence of Multiple Sclerosis

The present invention also features a kit for detecting the presence of multiple sclerosis or a risk of multiple sclerosis in a circulating phagocyte sample derived from a mammal. The kit comprises an antibody that binds to a multiple sclerosis-associated biomarker. In some embodiments, the kit further comprises a means for detecting the binding of the antibody to the multiple sclerosis-associated biomarker/antigen in the sample (e.g., an antibody-antigen complex). In some embodiments, the detecting of an elevated level of an antibody-antigen complex indicates presence of multiple sclerosis or a risk of multiple sclerosis.

In some embodiments, the kit comprises an antibody, wherein the antibody is a monoclonal or a polyclonal antibody. In some embodiments, the antibody is derived from a human, a mouse, a rat, a llama, a rabbit, a dog, a primate, a guinea pig, a cat, a hamster, a pig, a chicken, a goat, a horse, or a cow. In some embodiments, the antibody is humanized. In some embodiments, the antibody is a chimera. In some embodiments, the antibody is specific for the multiple sclerosis-associated biomarker.

Example 1

Detecting Multiple Sclerosis in a Patient

The following example describes the detection of multiple sclerosis in a patient according to two methods disclosed in the present invention. A 24-year-old male patient presents to his primary care physician complaining of changes in vision, limb weakness, and extreme fatigue. He mentions his symptoms have been recurring over the last 3 months. The physician suspects the possibility of a tumor in the central nervous system (CNS) or a CNS disease, as well as multiple sclerosis. The physician obtains a blood sample to be sent to a diagnostic laboratory for multiple sclerosis testing, and also refers the patient to a neurologist.

The laboratory receives the patient's blood sample collected in a CPT tube. PBMCs are obtained from a BD Vacutainer™ CPT tube using a cell separation procedure. The cells are washed three times in 1×PBS and centrifuged in a horizontal rotor (swing-out head) for a minimum of 5 minutes at 1200 to 1500 RCF (Relative Centrifugal force). The supernatant is removed and the cells are resuspended in 1×PBS. After the final wash, extracts of the PBMCs are prepared by lysing with a hypotonic solution or other method. Then the lysate is subjected to assay involving an antibody that binds to Tau protein fragment comprising the phosphorylated serine residue Ser-404. The assay indicates that an elevated level of said Tau protein fragment is present in the PBMCs. The assay is the assay of example 2 or example 3. Thus, the results of the assay indicate that the patient has multiple sclerosis. The physician notifies the patient, who then begins treatment immediately.

The laboratory receives the patient's blood sample collected in a CPT tube. PBMCs are obtained from a BD Vacutainer™ CPT tube using a cell separation procedure. The cells are washed three times in 1×PBS and centrifuged in a horizontal rotor (swing-out head) for a minimum of 5 minutes at 1200 to 1500 RCF (Relative Centrifugal force). The supernatant is removed and the cells are resuspended in 1×PBS. The cells are then subjected to assay involving an antibody that binds to Tau protein fragment comprising the phosphorylated serine residue Ser-404. The assay is the assay of example 4.

Example 2

Direct ELISA Assay Protocol

The following example describes a direct ELISA assay used for detecting a multiple sclerosis-associated antigen in a sample. The protein concentration of the sample is determined using the BioRad™ (Bradford method) assay. MicroELISA plates are coated by addition of 100 µL of a 5-20 µg/mL solution of the sample, which is then incubated for 1 hour at 21° C. The wells are washed out with phosphate buffered solution (PBS) with 0.05% polysorbate (Tween 20™). The wells are then filled with 0.1 M glycine in PBS and incubated for 1 hour at 21° C. to block unoccupied binding sites. After rewashing the wells, 100 µL of an appropriate dilution of antibody in PBS-0.05% Tween™ 20 with 1% bovine serum albumin (BSA) is added and incubated for 1 hour at 21° C. The unbound antibody is then washed out with three exchanges of PBS-0.05% Tween™ 20. One hundred µL of an appropriately diluted horse radish peroxidase conjugated anti-immunoglobulin G (IgG) in PBS-0.05% Tween™ 20-1% BSA is then added to each well and incubated for 1 hour at 21° C. The wells are then washed twice with PBS-0.05% Tween™ 20 and finally with PBS. One hundred µL of soluble MTB substrate solution is added to each well and incubated for 30 minutes at 21° C. after which 100 µL of MTB stop reagent is added and the color intensity is measured at 450 nm using an ELISA plate reader.

Appropriate dilutions of the antigen and antibody are established by performing checkerboard titrations. Antigen concentrations in samples are interpolated from standard curves.

Example 3

Indirect ELISA Assay Protocol

The following example describes an indirect ELISA assay used for detecting a multiple sclerosis-associated antigen in various samples. This assay is constructed using polyclonal and monoclonal antibodies. ELISA wells are coated with polyclonal antibody at an appropriate concentration and the wells are washed and blocked as described above. Various dilutions of antigen containing samples are added to the wells and incubated for 1 hour at 21° C., after which the wells are washed 3 times with PBS-0.05% Tween™ 20. The monoclonal antibody is then added at an appropriate dilution in PBS-0.05% Tween™20-1% BSA and incubated for 1 hour at 21° C. The wells are then washed 3 times and an appropriately diluted horse radish peroxidase conjugated anti-mouse IgM in PBS-0.05% Tween™20-1% BSA is then added to each well and incubated for 1 hour at 21° C. The wells are then washed twice with PBS-0.05% Tween™20 and finally with PBS. One hundred μL of soluble MTB substrate solution is added to each well and incubated for 30 minutes at 21° C. after which 100 μL of MTB stop reagent is added and the color intensity is measured at 450 nm using an ELISA plate reader.

Appropriate dilutions of antigen and antibody are established by performing checkerboard titrations. Antigen concentrations in samples are interpolated from standard curves.

Example 4

Flow Cytometry Protocol

The following example describes a flow cytometry assay used for detecting a multiple sclerosis-associated antigen in various samples. PBMCs from multiple sclerosis (MS) subjects and control subjects are stained with fluorescent antibodies to the multiple sclerosis-associated antigen (e.g., Tau protein) and also with fluorescent labeled antibodies to cluster designation (CD) 3 T-lymphocyte marker or CD 19 B-Lymphocyte marker, CD68 intracellular monocyte marker and CD14 monocyte/macrophage cell surface marker. The labeled cells are analyzed by flow cytometry for qualitative or quantitative differences.

PBMCs are obtained from a BD Vacutainer™ CPT tube using a cell separation procedure. The cells are washed three times in 1×PBS and centrifuged in a horizontal rotor (swing-out head) for a minimum of 5 minutes at 1200 to 1500 RCF (Relative Centrifugal force). The supernatant is removed and the cells are resuspended in 1×PBS. After the final wash, the cells are resuspended to approximately 4.0 mL in 1×PBS. Approximately 50 μL of the cell suspension to be analyzed is transferred into tubes for double staining with selected antibody pairs. Ten μL of 40 mg/mL normal human IgG (Sigma-Aldrich) for a total of 400 μg is added to each tube to block FC binding. The appropriate cell surface monoclonal antibodies CD3 PE, CD19 PE or CD14 PE are added at this time and incubated for 20 minutes at room temperature.

One hundred μl of Dako Intrastain™ Reagent A (fixative) is added to each tube and then mixed gently with a vortex mixer to ensure that the cells are in suspension. Cells are incubated at room temperature for 15 minutes. Two mL of 1×PBS working solution is added to each test tube and mixed gently. The tubes are centrifuged at 300×g for 5 minutes. Supernatant is aspirated leaving about 50 μl of fluid. The fluid is mixed thoroughly to ensure that the cells are in suspension.

One hundred μL of Dako Intrastain™ Reagent B (permeabilization) is added to each tube. The appropriate amount of the antibody specific for the multiple sclerosis-associated antigen is added to the appropriate tubes. The tubes are mixed gently to ensure that the cells are in suspension and incubated at room temperature for 15-60 minutes. Two mL of 1×PBS working solution is added to each test tube and mixed gently. The tubes are centrifuged at 300×g for 5 minutes, and then the supernatant is aspirated, leaving approximately 50 μl of fluid. The fluid is mixed thoroughly to ensure that the cells are in suspension.

One hundred μL of Dako Intrastain™ Reagent B (permeabilization) is added to each tube. The appropriate volume of the 2nd step antibody conjugated to FITC (specific to the multiple sclerosis-associated antigen) is added to the appropriate tubes. The tubes are mixed gently to ensure that the cells are in suspension and incubated at room temperature for 15-60 minutes. To each tube, 2.0 mLs of 1×PBS working solution is added. The tubes are mixed gently then centrifuged at 300×g for 5 minutes. The supernatant is aspirated, leaving approximately 50 μl of fluid. The tubes are mixed thoroughly to ensure that the cells are in suspension.

The pellet is resuspended in an appropriate volume of fluid for flow cytometry analysis. The sample is analyzed on a flow cytometer within 24-48 hours. For analysis, the gate is on the monocyte population and the data is collected in list mode. Qualitative and or quantitative differences are determined between normal and MS patients using the analysis software. Optimization steps include varying incubation time with antibodies, fixation time and permeabilization time.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A method of detecting multiple sclerosis in a patient, the method comprises:

(a) obtaining from the patient a fluid sample from outside of a brain tissue of the patient, the fluid sample comprises a blood sample or a cerebrospinal fluid sample, the fluid sample contains a circulating phagocyte; and (b) detecting a multiple sclerosis-associated biomarker in the phagocyte, the biomarker is a neural-specific biomarker comprising Tau, a fragment of Tau, phosphorylated Tau, hippocalcin-1, or 14-3-3 protein;

wherein detecting the biomarker in the phagocyte obtained from the fluid sample at a level higher than that of a control is indicative that the patient has multiple sclerosis.

* * * * *

SEQUENCE LISTING

<160> NUMBER OF SEQ ID NOS: 80

<210> SEQ ID NO 1
<211> LENGTH: 758
<212> TYPE: PRT
<213> ORGANISM: Human

<400> SEQUENCE: 1

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Glu Pro Glu Ser
            115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Leu Lys Gly Ala Gly Gly
    195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
            275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
            355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430
```

-continued

```
Pro Glu Pro Pro Ser Ser Pro Lys His Val Ser Ser Val Thr Ser Arg
            435                 440                 445

Thr Gly Ser Ser Gly Ala Lys Glu Met Lys Leu Lys Gly Ala Asp Gly
        450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
                500                 505                 510

Gly Tyr Ser Ser Pro Gly Ser Pro Gly Thr Pro Gly Ser Arg Ser Arg
            515                 520                 525

Thr Pro Ser Leu Pro Thr Pro Pro Thr Arg Glu Pro Lys Lys Val Ala
        530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
                580                 585                 590

Gln Ile Ile Asn Lys Lys Leu Asp Leu Ser Asn Val Gln Ser Lys Cys
            595                 600                 605

Gly Ser Lys Asp Asn Ile Lys His Val Pro Gly Gly Gly Ser Val Gln
        610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys Leu Asp Phe Lys Asp Arg Val Gln Ser Lys Ile Gly
                660                 665                 670

Ser Leu Asp Asn Ile Thr His Val Pro Gly Gly Gly Asn Lys Lys Ile
            675                 680                 685

Glu Thr His Lys Leu Thr Phe Arg Glu Asn Ala Lys Ala Lys Thr Asp
        690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser Thr Gly Ser Ile Asp Met
                725                 730                 735

Val Asp Ser Pro Gln Leu Ala Thr Leu Ala Asp Glu Val Ser Ala Ser
                740                 745                 750

Leu Ala Lys Gln Gly Leu
            755

<210> SEQ ID NO 2
<211> LENGTH: 10
<212> TYPE: PRT
<213> ORGANISM: Human

<400> SEQUENCE: 2

Met Ala Glu Pro Arg Gln Glu Phe Glu Val
1               5                   10

<210> SEQ ID NO 3
<211> LENGTH: 20
<212> TYPE: PRT
<213> ORGANISM: Human
```

<400> SEQUENCE: 3

Met Ala Glu Pro Arg Gln Glu Phe Glu Val Met Glu Asp His Ala Gly
1               5                   10                  15

Thr Tyr Gly Leu
            20

<210> SEQ ID NO 4
<211> LENGTH: 30
<212> TYPE: PRT
<213> ORGANISM: Human

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr
            20                  25                  30

<210> SEQ ID NO 5
<211> LENGTH: 40
<212> TYPE: PRT
<213> ORGANISM: Human

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp
            35                  40

<210> SEQ ID NO 6
<211> LENGTH: 50
<212> TYPE: PRT
<213> ORGANISM: Human

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
            35                  40                  45

Gln Thr
    50

<210> SEQ ID NO 7
<211> LENGTH: 60
<212> TYPE: PRT
<213> ORGANISM: Human

<400> SEQUENCE: 7

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly
    50                  55                  60

<210> SEQ ID NO 8
<211> LENGTH: 70
<212> TYPE: PRT
<213> ORGANISM: Human

<400> SEQUENCE: 8

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro
65                  70

<210> SEQ ID NO 9
<211> LENGTH: 80
<212> TYPE: PRT
<213> ORGANISM: Human

<400> SEQUENCE: 9

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

<210> SEQ ID NO 10
<211> LENGTH: 90
<212> TYPE: PRT
<213> ORGANISM: Human

<400> SEQUENCE: 10

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala
                85                  90

<210> SEQ ID NO 11
<211> LENGTH: 100
<212> TYPE: PRT
<213> ORGANISM: Human

<400> SEQUENCE: 11

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly
            100
```

<210> SEQ ID NO 12
<211> LENGTH: 110
<212> TYPE: PRT
<213> ORGANISM: Human

<400> SEQUENCE: 12

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp
            100                 105                 110
```

<210> SEQ ID NO 13
<211> LENGTH: 120
<212> TYPE: PRT
<213> ORGANISM: Human

<400> SEQUENCE: 13

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly
```

```
<210> SEQ ID NO 14
<211> LENGTH: 130
<212> TYPE: PRT
<213> ORGANISM: Human

<400> SEQUENCE: 14
```

| Met | Ala | Glu | Pro | Arg | Gln | Glu | Phe | Glu | Val | Met | Glu | Asp | His | Ala | Gly |
|---|---|---|---|---|---|---|---|---|---|---|---|---|---|---|---|
| 1 | | | | 5 | | | | | 10 | | | | | 15 | |

| Thr | Tyr | Gly | Leu | Gly | Asp | Arg | Lys | Asp | Gln | Gly | Gly | Tyr | Thr | Met | His |
|---|---|---|---|---|---|---|---|---|---|---|---|---|---|---|---|
| | | | 20 | | | | | 25 | | | | | 30 | | |

| Gln | Asp | Gln | Glu | Gly | Asp | Thr | Asp | Ala | Gly | Leu | Lys | Glu | Ser | Pro | Leu |
|---|---|---|---|---|---|---|---|---|---|---|---|---|---|---|---|
| | | 35 | | | | | 40 | | | | | 45 | | | |

| Gln | Thr | Pro | Thr | Glu | Asp | Gly | Ser | Glu | Glu | Pro | Gly | Ser | Glu | Thr | Ser |
|---|---|---|---|---|---|---|---|---|---|---|---|---|---|---|---|
| | 50 | | | | | 55 | | | | | 60 | | | | |

| Asp | Ala | Lys | Ser | Thr | Pro | Thr | Ala | Glu | Asp | Val | Thr | Ala | Pro | Leu | Val |
|---|---|---|---|---|---|---|---|---|---|---|---|---|---|---|---|
| 65 | | | | | 70 | | | | | 75 | | | | | 80 |

| Asp | Glu | Gly | Ala | Pro | Gly | Lys | Gln | Ala | Ala | Gln | Pro | His | Thr | Glu |
|---|---|---|---|---|---|---|---|---|---|---|---|---|---|---|
| | | | | 85 | | | | | 90 | | | | | 95 |

| Ile | Pro | Glu | Gly | Thr | Thr | Ala | Glu | Glu | Ala | Gly | Ile | Gly | Asp | Thr | Pro |
|---|---|---|---|---|---|---|---|---|---|---|---|---|---|---|---|
| | | | | 100 | | | | | 105 | | | | | 110 | |

| Ser | Leu | Glu | Asp | Glu | Ala | Ala | Gly | His | Val | Thr | Gln | Glu | Pro | Glu | Ser |
|---|---|---|---|---|---|---|---|---|---|---|---|---|---|---|---|
| | | | 115 | | | | | 120 | | | | | 125 | | |

| Gly | Lys |
|---|---|
| | 130 |

```
<210> SEQ ID NO 15
<211> LENGTH: 140
<212> TYPE: PRT
<213> ORGANISM: Human

<400> SEQUENCE: 15
```

| Met | Ala | Glu | Pro | Arg | Gln | Glu | Phe | Glu | Val | Met | Glu | Asp | His | Ala | Gly |
|---|---|---|---|---|---|---|---|---|---|---|---|---|---|---|---|
| 1 | | | | 5 | | | | | 10 | | | | | 15 | |

| Thr | Tyr | Gly | Leu | Gly | Asp | Arg | Lys | Asp | Gln | Gly | Gly | Tyr | Thr | Met | His |
|---|---|---|---|---|---|---|---|---|---|---|---|---|---|---|---|
| | | | 20 | | | | | 25 | | | | | 30 | | |

| Gln | Asp | Gln | Glu | Gly | Asp | Thr | Asp | Ala | Gly | Leu | Lys | Glu | Ser | Pro | Leu |
|---|---|---|---|---|---|---|---|---|---|---|---|---|---|---|---|
| | | 35 | | | | | 40 | | | | | 45 | | | |

| Gln | Thr | Pro | Thr | Glu | Asp | Gly | Ser | Glu | Glu | Pro | Gly | Ser | Glu | Thr | Ser |
|---|---|---|---|---|---|---|---|---|---|---|---|---|---|---|---|
| | 50 | | | | | 55 | | | | | 60 | | | | |

| Asp | Ala | Lys | Ser | Thr | Pro | Thr | Ala | Glu | Asp | Val | Thr | Ala | Pro | Leu | Val |
|---|---|---|---|---|---|---|---|---|---|---|---|---|---|---|---|
| 65 | | | | | 70 | | | | | 75 | | | | | 80 |

| Asp | Glu | Gly | Ala | Pro | Gly | Lys | Gln | Ala | Ala | Gln | Pro | His | Thr | Glu |
|---|---|---|---|---|---|---|---|---|---|---|---|---|---|---|
| | | | | 85 | | | | | 90 | | | | | 95 |

| Ile | Pro | Glu | Gly | Thr | Thr | Ala | Glu | Glu | Ala | Gly | Ile | Gly | Asp | Thr | Pro |
|---|---|---|---|---|---|---|---|---|---|---|---|---|---|---|---|
| | | | | 100 | | | | | 105 | | | | | 110 | |

| Ser | Leu | Glu | Asp | Glu | Ala | Ala | Gly | His | Val | Thr | Gln | Glu | Pro | Glu | Ser |
|---|---|---|---|---|---|---|---|---|---|---|---|---|---|---|---|
| | | | 115 | | | | | 120 | | | | | 125 | | |

| Gly | Lys | Val | Val | Gln | Glu | Gly | Phe | Leu | Arg | Glu | Pro |
|---|---|---|---|---|---|---|---|---|---|---|---|
| | 130 | | | | | 135 | | | | | 140 |

```
<210> SEQ ID NO 16
<211> LENGTH: 150
<212> TYPE: PRT
<213> ORGANISM: Human

<400> SEQUENCE: 16
```

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met
145                 150

<210> SEQ ID NO 17
<211> LENGTH: 160
<212> TYPE: PRT
<213> ORGANISM: Human

<400> SEQUENCE: 17

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

<210> SEQ ID NO 18
<211> LENGTH: 170
<212> TYPE: PRT
<213> ORGANISM: Human

<400> SEQUENCE: 18

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
```

```
              20                  25                  30
Gln Asp Gln Glu Gly Asp Thr Asp Ala Gly Leu Lys Glu Ser Pro Leu
            35                  40                  45
Gln Thr Pro Thr Glu Asp Gly Ser Glu Glu Pro Gly Ser Glu Thr Ser
        50                  55                  60
Asp Ala Lys Ser Thr Pro Thr Ala Glu Asp Val Thr Ala Pro Leu Val
65                  70                  75                  80
Asp Glu Gly Ala Pro Gly Lys Gln Ala Ala Gln Pro His Thr Glu
                85                  90                  95
Ile Pro Glu Gly Thr Thr Ala Glu Glu Ala Gly Ile Gly Asp Thr Pro
            100                 105                 110
Ser Leu Glu Asp Glu Ala Ala Gly His Val Thr Gln Glu Pro Glu Ser
        115                 120                 125
Gly Lys Val Val Gln Glu Gly Phe Leu Arg Glu Pro Gly Pro Pro Gly
    130                 135                 140
Leu Ser His Gln Leu Met Ser Gly Met Pro Gly Ala Pro Leu Leu Pro
145                 150                 155                 160
Glu Gly Pro Arg Glu Ala Thr Arg Gln Pro
                165                 170

<210> SEQ ID NO 19
<211> LENGTH: 180
<212> TYPE: PRT
<213> ORGANISM: Human

<400> SEQUENCE: 19

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
            20                  25                  30
Gln Asp Gln Glu Gly Asp Thr Asp Ala Gly Leu Lys Glu Ser Pro Leu
        35                  40                  45
Gln Thr Pro Thr Glu Asp Gly Ser Glu Glu Pro Gly Ser Glu Thr Ser
    50                  55                  60
Asp Ala Lys Ser Thr Pro Thr Ala Glu Asp Val Thr Ala Pro Leu Val
65                  70                  75                  80
Asp Glu Gly Ala Pro Gly Lys Gln Ala Ala Gln Pro His Thr Glu
                85                  90                  95
Ile Pro Glu Gly Thr Thr Ala Glu Glu Ala Gly Ile Gly Asp Thr Pro
            100                 105                 110
Ser Leu Glu Asp Glu Ala Ala Gly His Val Thr Gln Glu Pro Glu Ser
        115                 120                 125
Gly Lys Val Val Gln Glu Gly Phe Leu Arg Glu Pro Gly Pro Pro Gly
    130                 135                 140
Leu Ser His Gln Leu Met Ser Gly Met Pro Gly Ala Pro Leu Leu Pro
145                 150                 155                 160
Glu Gly Pro Arg Glu Ala Thr Arg Gln Pro Ser Gly Thr Gly Pro Glu
                165                 170                 175
Asp Thr Glu Gly
            180

<210> SEQ ID NO 20
<211> LENGTH: 190
<212> TYPE: PRT
<213> ORGANISM: Human

<400> SEQUENCE: 20
```

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His
            180                 185                 190

<210> SEQ ID NO 21
<211> LENGTH: 200
<212> TYPE: PRT
<213> ORGANISM: Human

<400> SEQUENCE: 21

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly
        195                 200

<210> SEQ ID NO 22
<211> LENGTH: 210
<212> TYPE: PRT
<213> ORGANISM: Human

<400> SEQUENCE: 22

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu
    210

<210> SEQ ID NO 23
<211> LENGTH: 220
<212> TYPE: PRT
<213> ORGANISM: Human

<400> SEQUENCE: 23

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

```
Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
            115                 120                 125

Gly Lys Val Val Gln Glu Gly Phe Leu Arg Glu Pro Gly Pro Pro Gly
            130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
            195                 200                 205

Lys Glu Arg Pro Gly Ser Lys Glu Glu Val Asp Glu
210                 215                 220

<210> SEQ ID NO 24
<211> LENGTH: 230
<212> TYPE: PRT
<213> ORGANISM: Human

<400> SEQUENCE: 24

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
            115                 120                 125

Gly Lys Val Val Gln Glu Gly Phe Leu Arg Glu Pro Gly Pro Pro Gly
            130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
            195                 200                 205

Lys Glu Arg Pro Gly Ser Lys Glu Glu Val Asp Glu Asp Arg Asp Val
210                 215                 220

Asp Glu Ser Ser Pro Gln
225                 230

<210> SEQ ID NO 25
<211> LENGTH: 240
```

```
<212> TYPE: PRT
<213> ORGANISM: Human

<400> SEQUENCE: 25

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Ala Gly Ile Gly Asp Thr Pro
            100                 105                 110

Ser Leu Glu Asp Glu Ala Ala Gly His Val Thr Gln Glu Pro Glu Ser
            115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

<210> SEQ ID NO 26
<211> LENGTH: 250
<212> TYPE: PRT
<213> ORGANISM: Human

<400> SEQUENCE: 26

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Ala Gly Ile Gly Asp Thr Pro
            100                 105                 110

Ser Leu Glu Asp Glu Ala Ala Gly His Val Thr Gln Glu Pro Glu Ser
```

```
              115                 120                 125
Gly Lys Val Val Gln Glu Gly Phe Leu Arg Glu Pro Gly Pro Gly
130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
                180                 185                 190

Leu Gly Asp Leu His Gln Glu Gly Pro Pro Leu Lys Gly Ala Gly Gly
                195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala
                245                 250

<210> SEQ ID NO 27
<211> LENGTH: 260
<212> TYPE: PRT
<213> ORGANISM: Human

<400> SEQUENCE: 27

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Gly
130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
                180                 185                 190

Leu Gly Asp Leu His Gln Glu Gly Pro Pro Leu Lys Gly Ala Gly Gly
                195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
```

```
                    245                 250                 255

Pro Gly Phe Pro
            260

<210> SEQ ID NO 28
<211> LENGTH: 270
<212> TYPE: PRT
<213> ORGANISM: Human

<400> SEQUENCE: 28

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp
            260                 265                 270

<210> SEQ ID NO 29
<211> LENGTH: 280
<212> TYPE: PRT
<213> ORGANISM: Human

<400> SEQUENCE: 29

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45
```

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro
        275                 280

<210> SEQ ID NO 30
<211> LENGTH: 290
<212> TYPE: PRT
<213> ORGANISM: Human

<400> SEQUENCE: 30

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

```
Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
                195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
                275                 280                 285

Val Gly
    290

<210> SEQ ID NO 31
<211> LENGTH: 300
<212> TYPE: PRT
<213> ORGANISM: Human

<400> SEQUENCE: 31

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
                195                 200                 205

Lys Glu Arg Pro Gly Ser Lys Glu Glu Val Asp Glu Asp Arg Asp Val
210                 215                 220
```

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
            245                 250                 255

Pro Gly Phe Pro Ala Glu Gly Ala Ile Pro Leu Pro Val Asp Phe Leu
        260                 265                 270

Ser Lys Val Ser Thr Glu Ile Pro Ala Ser Glu Pro Asp Gly Pro Ser
            275                 280                 285

Val Gly Arg Ala Lys Gly Gln Asp Ala Pro Leu Glu
        290                 295                 300

<210> SEQ ID NO 32
<211> LENGTH: 310
<212> TYPE: PRT
<213> ORGANISM: Human

<400> SEQUENCE: 32

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
            85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
            165                 170                 175

Asp Thr Glu Gly Gly Arg His Ala Pro Glu Leu Leu Lys His Gln Leu
        180                 185                 190

Leu Gly Asp Leu His Gln Glu Gly Pro Pro Leu Lys Gly Ala Gly Gly
    195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
            245                 250                 255

Pro Gly Phe Pro Ala Glu Gly Ala Ile Pro Leu Pro Val Asp Phe Leu
        260                 265                 270

Ser Lys Val Ser Thr Glu Ile Pro Ala Ser Glu Pro Asp Gly Pro Ser
            275                 280                 285

Val Gly Arg Ala Lys Gly Gln Asp Ala Pro Leu Glu Phe Thr Phe His
        290                 295                 300

```
Val Glu Ile Thr Pro Asn
305                 310

<210> SEQ ID NO 33
<211> LENGTH: 320
<212> TYPE: PRT
<213> ORGANISM: Human

<400> SEQUENCE: 33

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

<210> SEQ ID NO 34
<211> LENGTH: 330
<212> TYPE: PRT
<213> ORGANISM: Human

<400> SEQUENCE: 34
```

```
Met Ala Glu Pro Arg Gln Glu Phe Glu Val Met Glu Asp His Ala Gly
  1               5                  10                  15

Thr Tyr Gly Leu Gly Asp Arg Lys Asp Gln Gly Gly Tyr Thr Met His
             20                  25                  30

Gln Asp Gln Glu Gly Asp Thr Asp Ala Gly Leu Lys Glu Ser Pro Leu
         35                  40                  45

Gln Thr Pro Thr Glu Asp Gly Ser Glu Glu Pro Gly Ser Glu Thr Ser
     50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
             85                  90                  95

Ile Pro Glu Gly Thr Thr Ala Glu Glu Ala Gly Ile Gly Asp Thr Pro
         100                 105                 110

Ser Leu Glu Asp Glu Ala Ala Gly His Val Thr Gln Glu Pro Glu Ser
         115                 120                 125

Gly Lys Val Val Gln Glu Gly Phe Leu Arg Glu Pro Gly Pro Pro Gly
         130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
             165                 170                 175

Asp Thr Glu Gly Gly Arg His Ala Pro Glu Leu Leu Lys His Gln Leu
         180                 185                 190

Leu Gly Asp Leu His Gln Glu Gly Pro Pro Leu Lys Gly Ala Gly Gly
         195                 200                 205

Lys Glu Arg Pro Gly Ser Lys Glu Glu Val Asp Glu Asp Arg Asp Val
         210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
             245                 250                 255

Pro Gly Phe Pro Ala Glu Gly Ala Ile Pro Leu Pro Val Asp Phe Leu
         260                 265                 270

Ser Lys Val Ser Thr Glu Ile Pro Ala Ser Glu Pro Asp Gly Pro Ser
         275                 280                 285

Val Gly Arg Ala Lys Gly Gln Asp Ala Pro Leu Glu Phe Thr Phe His
         290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala
             325                 330

<210> SEQ ID NO 35
<211> LENGTH: 340
<212> TYPE: PRT
<213> ORGANISM: Human

<400> SEQUENCE: 35

Met Ala Glu Pro Arg Gln Glu Phe Glu Val Met Glu Asp His Ala Gly
  1               5                  10                  15

Thr Tyr Gly Leu Gly Asp Arg Lys Asp Gln Gly Gly Tyr Thr Met His
             20                  25                  30

Gln Asp Gln Glu Gly Asp Thr Asp Ala Gly Leu Lys Glu Ser Pro Leu
         35                  40                  45
```

```
Gln Thr Pro Thr Glu Asp Gly Ser Glu Glu Pro Gly Ser Glu Thr Ser
     50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Glu Pro Glu Ser
                115                 120                 125

Gly Lys Val Val Gln Glu Gly Phe Leu Arg Glu Pro Gly Pro Pro Gly
                130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
                180                 185                 190

Leu Gly Asp Leu His Gln Glu Gly Pro Pro Leu Lys Gly Ala Gly Gly
                195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
                260                 265                 270

Ser Lys Val Ser Thr Glu Ile Pro Ala Ser Glu Pro Asp Gly Pro Ser
                275                 280                 285

Val Gly Arg Ala Lys Gly Gln Asp Ala Pro Leu Glu Phe Thr Phe His
                290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro
                340

<210> SEQ ID NO 36
<211> LENGTH: 350
<212> TYPE: PRT
<213> ORGANISM: Human

<400> SEQUENCE: 36

Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
                 20                  25                  30

Gln Asp Gln Glu Gly Asp Thr Asp Ala Gly Leu Lys Glu Ser Pro Leu
                 35                  40                  45

Gln Thr Pro Thr Glu Asp Gly Ser Glu Glu Pro Gly Ser Glu Thr Ser
     50                  55                  60

Asp Ala Lys Ser Thr Pro Thr Ala Glu Asp Val Thr Ala Pro Leu Val
 65                  70                  75                  80
```

-continued

Asp Glu Gly Ala Pro Gly Lys Gln Ala Ala Gln Pro His Thr Glu
                85                  90                  95

Ile Pro Glu Gly Thr Thr Ala Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
        130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
        210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
        290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp
                340                 345                 350

<210> SEQ ID NO 37
<211> LENGTH: 360
<212> TYPE: PRT
<213> ORGANISM: Human

<400> SEQUENCE: 37

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

```
Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Val Asp Glu Asp Arg Asp Val
    210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala
        355                 360

<210> SEQ ID NO 38
<211> LENGTH: 370
<212> TYPE: PRT
<213> ORGANISM: Human

<400> SEQUENCE: 38

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125
```

```
Gly Lys Val Val Gln Glu Gly Phe Leu Arg Glu Pro Gly Pro Gly
            130                 135                 140
Leu Ser His Gln Leu Met Ser Gly Met Pro Gly Ala Pro Leu Leu Pro
145                 150                 155                 160
Glu Gly Pro Arg Glu Ala Thr Arg Gln Pro Ser Gly Thr Gly Pro Glu
                165                 170                 175
Asp Thr Glu Gly Gly Arg His Ala Pro Glu Leu Leu Lys His Gln Leu
            180                 185                 190
Leu Gly Asp Leu His Gln Gly Pro Pro Leu Lys Gly Ala Gly Gly
        195                 200                 205
Lys Glu Arg Pro Gly Ser Lys Glu Glu Val Asp Glu Asp Arg Asp Val
    210                 215                 220
Asp Glu Ser Ser Pro Gln Asp Ser Pro Ser Lys Ala Ser Pro Ala
225                 230                 235                 240
Gln Asp Gly Arg Pro Pro Gln Thr Ala Ala Arg Glu Ala Thr Ser Ile
                245                 250                 255
Pro Gly Phe Pro Ala Glu Gly Ala Ile Pro Leu Pro Val Asp Phe Leu
            260                 265                 270
Ser Lys Val Ser Thr Glu Ile Pro Ala Ser Glu Pro Asp Gly Pro Ser
        275                 280                 285
Val Gly Arg Ala Lys Gly Gln Asp Ala Pro Leu Glu Phe Thr Phe His
    290                 295                 300
Val Glu Ile Thr Pro Asn Val Gln Lys Glu Gln Ala His Ser Glu Glu
305                 310                 315                 320
His Leu Gly Arg Ala Ala Phe Pro Gly Ala Pro Gly Glu Gly Pro Glu
                325                 330                 335
Ala Arg Gly Pro Ser Leu Gly Glu Asp Thr Lys Glu Ala Asp Leu Pro
            340                 345                 350
Glu Pro Ser Glu Lys Gln Pro Ala Ala Ala Pro Arg Gly Lys Pro Val
        355                 360                 365
Ser Arg
    370

<210> SEQ ID NO 39
<211> LENGTH: 380
<212> TYPE: PRT
<213> ORGANISM: Human

<400> SEQUENCE: 39

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
            20                  25                  30
Gln Asp Gln Glu Gly Asp Thr Asp Ala Gly Leu Lys Glu Ser Pro Leu
        35                  40                  45
Gln Thr Pro Thr Glu Asp Gly Ser Glu Glu Pro Gly Ser Glu Thr Ser
    50                  55                  60
Asp Ala Lys Ser Thr Pro Thr Ala Glu Asp Val Thr Ala Pro Leu Val
65                  70                  75                  80
Asp Glu Gly Ala Pro Gly Lys Gln Ala Ala Ala Gln Pro His Thr Glu
                85                  90                  95
Ile Pro Glu Gly Thr Thr Ala Glu Glu Ala Gly Ile Gly Asp Thr Pro
            100                 105                 110
Ser Leu Glu Asp Glu Ala Ala Gly His Val Thr Gln Glu Pro Glu Ser
        115                 120                 125
```

```
Gly Lys Val Val Gln Glu Gly Phe Leu Arg Glu Pro Gly Pro Gly
        130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
                180                 185                 190

Leu Gly Asp Leu His Gln Gly Pro Pro Leu Lys Gly Ala Gly Gly
            195                 200                 205

Lys Glu Arg Pro Gly Ser Lys Glu Glu Val Asp Glu Asp Arg Asp Val
        210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
            275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
                340                 345                 350

Glu Pro Ser Glu Lys Gln Pro Ala Ala Ala Pro Arg Gly Lys Pro Val
                355                 360                 365

Ser Arg Val Pro Gln Leu Lys Ala Arg Met Val Ser
            370                 375                 380

<210> SEQ ID NO 40
<211> LENGTH: 390
<212> TYPE: PRT
<213> ORGANISM: Human

<400> SEQUENCE: 40

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Glu Pro Glu Ser
            115                 120                 125
```

Gly Lys Val Val Gln Glu Gly Phe Leu Arg Glu Pro Gly Pro Gly
130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
                180                 185                 190

Leu Gly Asp Leu His Gln Gly Gly Pro Pro Leu Lys Gly Ala Gly Gly
            195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
            275                 280                 285

Val Gly Arg Ala Lys Gly Gln Asp Ala Pro Leu Glu Phe Thr Phe His
290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
            355                 360                 365

Ser Arg Val Pro Gln Leu Lys Ala Arg Met Val Ser Lys Ser Lys Asp
            370                 375                 380

Gly Thr Gly Ser Asp Asp
385                 390

<210> SEQ ID NO 41
<211> LENGTH: 400
<212> TYPE: PRT
<213> ORGANISM: Human

<400> SEQUENCE: 41

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Ala Gly Ile Gly Asp Thr Pro
            100                 105                 110

```
Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

<210> SEQ ID NO 42
<211> LENGTH: 410
<212> TYPE: PRT
<213> ORGANISM: Human

<400> SEQUENCE: 42

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95
```

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu
                405                 410

<210> SEQ ID NO 43
<211> LENGTH: 420
<212> TYPE: PRT
<213> ORGANISM: Human

<400> SEQUENCE: 43

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

```
Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
            115                 120                 125

Gly Lys Val Val Gln Glu Gly Phe Leu Arg Glu Pro Gly Pro Pro Gly
        130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
            195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
            275                 280                 285

Val Gly Arg Ala Lys Gly Gln Asp Ala Pro Leu Glu Phe Thr Phe His
        290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
            355                 360                 365

Ser Arg Val Pro Gln Leu Lys Ala Arg Met Val Ser Lys Ser Lys Asp
        370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser
            420

<210> SEQ ID NO 44
<211> LENGTH: 430
<212> TYPE: PRT
<213> ORGANISM: Human

<400> SEQUENCE: 44

Met Ala Glu Pro Arg Gln Glu Phe Glu Val Met Glu Asp His Ala Gly
 1               5                  10                  15
```

```
Thr Tyr Gly Leu Gly Asp Arg Lys Asp Gln Gly Gly Tyr Thr Met His
             20                  25                  30

Gln Asp Gln Glu Gly Asp Thr Asp Ala Gly Leu Lys Glu Ser Pro Leu
         35                  40                  45

Gln Thr Pro Thr Glu Asp Gly Ser Glu Pro Gly Ser Glu Thr Ser
 50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Ala Gly Ile Gly Asp Thr Pro
                 100                 105                 110

Ser Leu Glu Asp Glu Ala Ala Gly His Val Thr Gln Glu Pro Glu Ser
         115                 120                 125

Gly Lys Val Val Gln Glu Gly Phe Leu Arg Glu Pro Gly Pro Pro Gly
         130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                 165                 170                 175

Asp Thr Glu Gly Gly Arg His Ala Pro Glu Leu Leu Lys His Gln Leu
                 180                 185                 190

Leu Gly Asp Leu His Gln Gly Gly Pro Pro Leu Lys Gly Ala Gly Gly
             195                 200                 205

Lys Glu Arg Pro Gly Ser Lys Glu Glu Val Asp Glu Asp Arg Asp Val
 210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                 245                 250                 255

Pro Gly Phe Pro Ala Glu Gly Ala Ile Pro Leu Pro Val Asp Phe Leu
                 260                 265                 270

Ser Lys Val Ser Thr Glu Ile Pro Ala Ser Glu Pro Asp Gly Pro Ser
             275                 280                 285

Val Gly Arg Ala Lys Gly Gln Asp Ala Pro Leu Glu Phe Thr Phe His
 290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                 325                 330                 335

Ala Arg Gly Pro Ser Leu Gly Glu Asp Thr Lys Glu Ala Asp Leu Pro
                 340                 345                 350

Glu Pro Ser Glu Lys Gln Pro Ala Ala Ala Pro Arg Gly Lys Pro Val
                 355                 360                 365

Ser Arg Val Pro Gln Leu Lys Ala Arg Met Val Ser Lys Ser Lys Asp
             370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                 405                 410                 415

Pro Gly Ser Ser Asp Pro Leu Ile Gln Pro Ser Ser Pro Ala
                 420                 425                 430

<210> SEQ ID NO 45
```

```
<211> LENGTH: 440
<212> TYPE: PRT
<213> ORGANISM: Human

<400> SEQUENCE: 45

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400
```

```
Ala Lys Thr Leu Lys Asn Arg Pro Cys Leu Ser Pro Lys Leu Pro Thr
                405                 410                 415
Pro Gly Ser Ser Asp Pro Leu Ile Gln Pro Ser Ser Pro Ala Val Cys
                420                 425                 430
Pro Glu Pro Pro Ser Ser Pro Lys
                435                 440

<210> SEQ ID NO 46
<211> LENGTH: 450
<212> TYPE: PRT
<213> ORGANISM: Human

<400> SEQUENCE: 46

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
                20                  25                  30
Gln Asp Gln Glu Gly Asp Thr Asp Ala Gly Leu Lys Glu Ser Pro Leu
            35                  40                  45
Gln Thr Pro Thr Glu Asp Gly Ser Glu Glu Pro Gly Ser Glu Thr Ser
        50                  55                  60
Asp Ala Lys Ser Thr Pro Thr Ala Glu Asp Val Thr Ala Pro Leu Val
65                  70                  75                  80
Asp Glu Gly Ala Pro Gly Lys Gln Ala Ala Ala Gln Pro His Thr Glu
                85                  90                  95
Ile Pro Glu Gly Thr Thr Ala Glu Ala Gly Ile Gly Asp Thr Pro
                100                 105                 110
Ser Leu Glu Asp Glu Ala Ala Gly His Val Thr Gln Glu Pro Glu Ser
            115                 120                 125
Gly Lys Val Val Gln Glu Gly Phe Leu Arg Glu Pro Gly Pro Pro Gly
        130                 135                 140
Leu Ser His Gln Leu Met Ser Gly Met Pro Gly Ala Pro Leu Leu Pro
145                 150                 155                 160
Glu Gly Pro Arg Glu Ala Thr Arg Gln Pro Ser Gly Thr Gly Pro Glu
                165                 170                 175
Asp Thr Glu Gly Gly Arg His Ala Pro Glu Leu Leu Lys His Gln Leu
                180                 185                 190
Leu Gly Asp Leu His Gln Glu Gly Pro Pro Leu Lys Gly Ala Gly Gly
            195                 200                 205
Lys Glu Arg Pro Gly Ser Lys Glu Glu Val Asp Glu Asp Arg Asp Val
        210                 215                 220
Asp Glu Ser Ser Pro Gln Asp Ser Pro Pro Ser Lys Ala Ser Pro Ala
225                 230                 235                 240
Gln Asp Gly Arg Pro Pro Gln Thr Ala Ala Arg Glu Ala Thr Ser Ile
                245                 250                 255
Pro Gly Phe Pro Ala Glu Gly Ala Ile Pro Leu Pro Val Asp Phe Leu
                260                 265                 270
Ser Lys Val Ser Thr Glu Ile Pro Ala Ser Glu Pro Asp Gly Pro Ser
            275                 280                 285
Val Gly Arg Ala Lys Gly Gln Asp Ala Pro Leu Glu Phe Thr Phe His
        290                 295                 300
Val Glu Ile Thr Pro Asn Val Gln Lys Glu Gln Ala His Ser Glu Glu
305                 310                 315                 320
His Leu Gly Arg Ala Ala Phe Pro Gly Ala Pro Gly Glu Gly Pro Glu
                325                 330                 335
```

Ala Arg Gly Pro Ser Leu Gly Glu Asp Thr Lys Glu Ala Asp Leu Pro
                340                 345                 350

Glu Pro Ser Glu Lys Gln Pro Ala Ala Pro Arg Gly Lys Pro Val
        355                 360                 365

Ser Arg Val Pro Gln Leu Lys Ala Arg Met Val Ser Lys Ser Lys Asp
        370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
                420                 425                 430

Pro Glu Pro Pro Ser Ser Pro Lys His Val Ser Ser Val Thr Ser Arg
                435                 440                 445

Thr Gly
    450

<210> SEQ ID NO 47
<211> LENGTH: 460
<212> TYPE: PRT
<213> ORGANISM: Human

<400> SEQUENCE: 47

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

```
Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys
    450                 455                 460

<210> SEQ ID NO 48
<211> LENGTH: 470
<212> TYPE: PRT
<213> ORGANISM: Human

<400> SEQUENCE: 48

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175
```

```
Asp Thr Glu Gly Gly Arg His Ala Pro Glu Leu Leu Lys His Gln Leu
            180                 185                 190

Leu Gly Asp Leu His Gln Gly Pro Pro Leu Lys Gly Ala Gly Gly
        195                 200                 205

Lys Glu Arg Pro Gly Ser Lys Glu Val Asp Glu Asp Arg Asp Val
    210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr
465                 470

<210> SEQ ID NO 49
<211> LENGTH: 480
<212> TYPE: PRT
<213> ORGANISM: Human

<400> SEQUENCE: 49

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80
```

```
Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
            115                 120                 125

Gly Lys Val Val Gln Glu Gly Phe Leu Arg Glu Pro Gly Pro Pro Gly
130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
            195                 200                 205

Lys Glu Arg Pro Gly Ser Lys Glu Val Asp Glu Arg Asp Val
210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
            275                 280                 285

Val Gly Arg Ala Lys Gly Gln Asp Ala Pro Leu Glu Phe Thr Phe His
            290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
            355                 360                 365

Ser Arg Val Pro Gln Leu Lys Ala Arg Met Val Ser Lys Ser Lys Asp
            370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Pro Ala Val Cys
            420                 425                 430

Pro Glu Pro Pro Ser Ser Pro Lys His Val Ser Ser Val Thr Ser Arg
            435                 440                 445

Thr Gly Ser Ser Gly Ala Lys Glu Met Lys Leu Lys Gly Ala Asp Gly
            450                 455                 460

Lys Thr Lys Ile Ala Thr Pro Arg Gly Ala Ala Pro Gly Gln Lys
465                 470                 475                 480

<210> SEQ ID NO 50
<211> LENGTH: 490
<212> TYPE: PRT
```

<213> ORGANISM: Human

<400> SEQUENCE: 50

| | | | | | | | | | | | | | | |
|---|---|---|---|---|---|---|---|---|---|---|---|---|---|---|
| Met | Ala | Glu | Pro | Arg | Gln | Glu | Phe | Glu | Val | Met | Glu | Asp | His | Ala | Gly |
| 1 | | | | 5 | | | | | 10 | | | | | 15 | |

| Thr | Tyr | Gly | Leu | Gly | Asp | Arg | Lys | Asp | Gln | Gly | Gly | Tyr | Thr | Met | His |
|---|---|---|---|---|---|---|---|---|---|---|---|---|---|---|---|
| | | | 20 | | | | | 25 | | | | | 30 | | |

| Gln | Asp | Gln | Glu | Gly | Asp | Thr | Asp | Ala | Gly | Leu | Lys | Glu | Ser | Pro | Leu |
|---|---|---|---|---|---|---|---|---|---|---|---|---|---|---|---|
| | | 35 | | | | | 40 | | | | | 45 | | | |

| Gln | Thr | Pro | Thr | Glu | Asp | Gly | Ser | Glu | Glu | Pro | Gly | Ser | Glu | Thr | Ser |
|---|---|---|---|---|---|---|---|---|---|---|---|---|---|---|---|
| 50 | | | | | 55 | | | | | 60 | | | | | |

| Asp | Ala | Lys | Ser | Thr | Pro | Thr | Ala | Glu | Asp | Val | Thr | Ala | Pro | Leu | Val |
|---|---|---|---|---|---|---|---|---|---|---|---|---|---|---|---|
| 65 | | | | | 70 | | | | | 75 | | | | | 80 |

| Asp | Glu | Gly | Ala | Pro | Gly | Lys | Gln | Ala | Ala | Gln | Pro | His | Thr | Glu |
|---|---|---|---|---|---|---|---|---|---|---|---|---|---|---|
| | | | | 85 | | | | | 90 | | | | | 95 |

| Ile | Pro | Glu | Gly | Thr | Thr | Ala | Glu | Glu | Ala | Gly | Ile | Gly | Asp | Thr | Pro |
|---|---|---|---|---|---|---|---|---|---|---|---|---|---|---|---|
| | | | | 100 | | | | | 105 | | | | | 110 | |

| Ser | Leu | Glu | Asp | Glu | Ala | Ala | Gly | His | Val | Thr | Gln | Glu | Pro | Glu | Ser |
|---|---|---|---|---|---|---|---|---|---|---|---|---|---|---|---|
| | | | 115 | | | | | 120 | | | | | 125 | | |

| Gly | Lys | Val | Val | Gln | Glu | Gly | Phe | Leu | Arg | Glu | Pro | Gly | Pro | Pro | Gly |
|---|---|---|---|---|---|---|---|---|---|---|---|---|---|---|---|
| | | 130 | | | | | 135 | | | | | 140 | | | |

| Leu | Ser | His | Gln | Leu | Met | Ser | Gly | Met | Pro | Gly | Ala | Pro | Leu | Leu | Pro |
|---|---|---|---|---|---|---|---|---|---|---|---|---|---|---|---|
| 145 | | | | | 150 | | | | | 155 | | | | | 160 |

| Glu | Gly | Pro | Arg | Glu | Ala | Thr | Arg | Gln | Pro | Ser | Gly | Thr | Gly | Pro | Glu |
|---|---|---|---|---|---|---|---|---|---|---|---|---|---|---|---|
| | | | | 165 | | | | | 170 | | | | | 175 | |

| Asp | Thr | Glu | Gly | Gly | Arg | His | Ala | Pro | Glu | Leu | Leu | Lys | His | Gln | Leu |
|---|---|---|---|---|---|---|---|---|---|---|---|---|---|---|---|
| | | | 180 | | | | | 185 | | | | | 190 | | |

| Leu | Gly | Asp | Leu | His | Gln | Glu | Gly | Pro | Pro | Leu | Lys | Gly | Ala | Gly | Gly |
|---|---|---|---|---|---|---|---|---|---|---|---|---|---|---|---|
| | | | 195 | | | | | 200 | | | | | 205 | | |

| Lys | Glu | Arg | Pro | Gly | Ser | Lys | Glu | Glu | Val | Asp | Glu | Asp | Arg | Asp | Val |
|---|---|---|---|---|---|---|---|---|---|---|---|---|---|---|---|
| | 210 | | | | | 215 | | | | | 220 | | | | |

| Asp | Glu | Ser | Ser | Pro | Gln | Asp | Ser | Pro | Pro | Ser | Lys | Ala | Ser | Pro | Ala |
|---|---|---|---|---|---|---|---|---|---|---|---|---|---|---|---|
| 225 | | | | | 230 | | | | | 235 | | | | | 240 |

| Gln | Asp | Gly | Arg | Pro | Pro | Gln | Thr | Ala | Ala | Arg | Glu | Ala | Thr | Ser | Ile |
|---|---|---|---|---|---|---|---|---|---|---|---|---|---|---|---|
| | | | | 245 | | | | | 250 | | | | | 255 | |

| Pro | Gly | Phe | Pro | Ala | Glu | Gly | Ala | Ile | Pro | Leu | Pro | Val | Asp | Phe | Leu |
|---|---|---|---|---|---|---|---|---|---|---|---|---|---|---|---|
| | | | 260 | | | | | 265 | | | | | 270 | | |

| Ser | Lys | Val | Ser | Thr | Glu | Ile | Pro | Ala | Ser | Glu | Pro | Asp | Gly | Pro | Ser |
|---|---|---|---|---|---|---|---|---|---|---|---|---|---|---|---|
| | | 275 | | | | | 280 | | | | | 285 | | | |

| Val | Gly | Arg | Ala | Lys | Gly | Gln | Asp | Ala | Pro | Leu | Glu | Phe | Thr | Phe | His |
|---|---|---|---|---|---|---|---|---|---|---|---|---|---|---|---|
| | 290 | | | | | 295 | | | | | 300 | | | | |

| Val | Glu | Ile | Thr | Pro | Asn | Val | Gln | Lys | Glu | Gln | Ala | His | Ser | Glu | Glu |
|---|---|---|---|---|---|---|---|---|---|---|---|---|---|---|---|
| 305 | | | | | 310 | | | | | 315 | | | | | 320 |

| His | Leu | Gly | Arg | Ala | Ala | Phe | Pro | Gly | Ala | Pro | Gly | Glu | Gly | Pro | Glu |
|---|---|---|---|---|---|---|---|---|---|---|---|---|---|---|---|
| | | | | 325 | | | | | 330 | | | | | 335 | |

| Ala | Arg | Gly | Pro | Ser | Leu | Gly | Glu | Asp | Thr | Lys | Glu | Ala | Asp | Leu | Pro |
|---|---|---|---|---|---|---|---|---|---|---|---|---|---|---|---|
| | | | 340 | | | | | 345 | | | | | 350 | | |

| Glu | Pro | Ser | Glu | Lys | Gln | Pro | Ala | Ala | Ala | Pro | Arg | Gly | Lys | Pro | Val |
|---|---|---|---|---|---|---|---|---|---|---|---|---|---|---|---|
| | | | 355 | | | | | 360 | | | | | 365 | | |

| Ser | Arg | Val | Pro | Gln | Leu | Lys | Ala | Arg | Met | Val | Ser | Lys | Ser | Lys | Asp |
|---|---|---|---|---|---|---|---|---|---|---|---|---|---|---|---|
| | 370 | | | | | 375 | | | | | 380 | | | | |

| Gly | Thr | Gly | Ser | Asp | Asp | Lys | Lys | Ala | Lys | Thr | Ser | Thr | Arg | Ser | Ser |
|---|---|---|---|---|---|---|---|---|---|---|---|---|---|---|---|
| 385 | | | | | 390 | | | | | 395 | | | | | 400 |

| Ala | Lys | Thr | Leu | Lys | Asn | Arg | Pro | Cys | Leu | Ser | Pro | Lys | Leu | Pro | Thr |
|---|---|---|---|---|---|---|---|---|---|---|---|---|---|---|---|

-continued

```
              405                 410                 415
Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
            435                 440                 445

Thr Gly Ser Ser Gly Ala Lys Glu Met Lys Leu Lys Gly Ala Asp Gly
            450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala
                485                 490

<210> SEQ ID NO 51
<211> LENGTH: 500
<212> TYPE: PRT
<213> ORGANISM: Human

<400> SEQUENCE: 51

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
```

```
                    290                 295                 300
Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
                340                 345                 350

Glu Pro Ser Glu Lys Gln Pro Ala Ala Ala Pro Arg Gly Lys Pro Val
                355                 360                 365

Ser Arg Val Pro Gln Leu Lys Ala Arg Met Val Ser Lys Ser Lys Asp
370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
                420                 425                 430

Pro Glu Pro Pro Ser Ser Pro Lys His Val Ser Ser Val Thr Ser Arg
                435                 440                 445

Thr Gly Ser Ser Gly Ala Lys Glu Met Lys Leu Lys Gly Ala Asp Gly
                450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro
                500

<210> SEQ ID NO 52
<211> LENGTH: 510
<212> TYPE: PRT
<213> ORGANISM: Human

<400> SEQUENCE: 52

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
                35                  40                  45

Gln Thr Pro Thr Glu Asp Gly Ser Glu Glu Pro Gly Ser Glu Thr Ser
                50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Glu Pro Glu Ser
                115                 120                 125

Gly Lys Val Val Gln Glu Gly Phe Leu Arg Glu Pro Gly Pro Pro Gly
                130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
```

```
                    165                 170                 175
Asp Thr Glu Gly Gly Arg His Ala Pro Glu Leu Leu Lys His Gln Leu
                180                 185                 190

Leu Gly Asp Leu His Gln Glu Gly Pro Pro Leu Lys Gly Ala Gly Gly
            195                 200                 205

Lys Glu Arg Pro Gly Ser Lys Glu Val Asp Glu Asp Arg Asp Val
        210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp
            500                 505                 510

<210> SEQ ID NO 53
<211> LENGTH: 520
<212> TYPE: PRT
<213> ORGANISM: Human

<400> SEQUENCE: 53

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
```

-continued

```
                35                  40                  45
Gln Thr Pro Thr Glu Asp Gly Ser Glu Pro Gly Ser Glu Thr Ser
             50                  55                  60
Asp Ala Lys Ser Thr Pro Thr Ala Glu Asp Val Thr Ala Pro Leu Val
 65                  70                  75                  80
Asp Glu Gly Ala Pro Gly Lys Gln Ala Ala Gln Pro His Thr Glu
                 85                  90                  95
Ile Pro Glu Gly Thr Thr Ala Glu Glu Ala Gly Ile Gly Asp Thr Pro
                100                 105                 110
Ser Leu Glu Asp Glu Ala Ala Gly His Val Thr Gln Glu Pro Glu Ser
            115                 120                 125
Gly Lys Val Val Gln Glu Gly Phe Leu Arg Glu Pro Gly Pro Pro Gly
        130                 135                 140
Leu Ser His Gln Leu Met Ser Gly Met Pro Gly Ala Pro Leu Leu Pro
145                 150                 155                 160
Glu Gly Pro Arg Glu Ala Thr Arg Gln Pro Ser Gly Thr Gly Pro Glu
                165                 170                 175
Asp Thr Glu Gly Gly Arg His Ala Pro Glu Leu Leu Lys His Gln Leu
            180                 185                 190
Leu Gly Asp Leu His Gln Glu Gly Pro Pro Leu Lys Gly Ala Gly Gly
        195                 200                 205
Lys Glu Arg Pro Gly Ser Lys Glu Glu Val Asp Glu Asp Arg Asp Val
210                 215                 220
Asp Glu Ser Ser Pro Gln Asp Ser Pro Ser Lys Ala Ser Pro Ala
225                 230                 235                 240
Gln Asp Gly Arg Pro Pro Gln Thr Ala Ala Arg Glu Ala Thr Ser Ile
                245                 250                 255
Pro Gly Phe Pro Ala Glu Gly Ala Ile Pro Leu Pro Val Asp Phe Leu
            260                 265                 270
Ser Lys Val Ser Thr Glu Ile Pro Ala Ser Glu Pro Asp Gly Pro Ser
        275                 280                 285
Val Gly Arg Ala Lys Gly Gln Asp Ala Pro Leu Glu Phe Thr Phe His
290                 295                 300
Val Glu Ile Thr Pro Asn Val Gln Lys Glu Gln Ala His Ser Glu Glu
305                 310                 315                 320
His Leu Gly Arg Ala Ala Phe Pro Gly Ala Pro Gly Glu Gly Pro Glu
                325                 330                 335
Ala Arg Gly Pro Ser Leu Gly Glu Asp Thr Lys Glu Ala Asp Leu Pro
            340                 345                 350
Glu Pro Ser Glu Lys Gln Pro Ala Ala Ala Pro Arg Gly Lys Pro Val
        355                 360                 365
Ser Arg Val Pro Gln Leu Lys Ala Arg Met Val Ser Lys Ser Lys Asp
    370                 375                 380
Gly Thr Gly Ser Asp Asp Lys Lys Ala Lys Thr Ser Thr Arg Ser Ser
385                 390                 395                 400
Ala Lys Thr Leu Lys Asn Arg Pro Cys Leu Ser Pro Lys Leu Pro Thr
                405                 410                 415
Pro Gly Ser Ser Asp Pro Leu Ile Gln Pro Ser Ser Pro Ala Val Cys
            420                 425                 430
Pro Glu Pro Pro Ser Pro Lys His Val Ser Ser Val Thr Ser Arg
        435                 440                 445
Thr Gly Ser Ser Gly Ala Lys Glu Met Lys Leu Lys Gly Ala Asp Gly
    450                 455                 460
```

```
Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro
            515                 520

<210> SEQ ID NO 54
<211> LENGTH: 530
<212> TYPE: PRT
<213> ORGANISM: Human

<400> SEQUENCE: 54

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320
```

-continued

```
His Leu Gly Arg Ala Ala Phe Pro Gly Ala Pro Gly Glu Gly Pro Glu
            325                 330                 335

Ala Arg Gly Pro Ser Leu Gly Glu Asp Thr Lys Glu Ala Asp Leu Pro
        340                 345                 350

Glu Pro Ser Glu Lys Gln Pro Ala Ala Ala Pro Arg Gly Lys Pro Val
            355                 360                 365

Ser Arg Val Pro Gln Leu Lys Ala Arg Met Val Ser Lys Ser Lys Asp
        370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
            405                 410                 415

Pro Gly Ser Ser Asp Pro Leu Ile Gln Pro Ser Ser Pro Ala Val Cys
        420                 425                 430

Pro Glu Pro Pro Ser Ser Pro Lys His Val Ser Ser Val Thr Ser Arg
            435                 440                 445

Thr Gly Ser Ser Gly Ala Lys Glu Met Lys Leu Lys Gly Ala Asp Gly
        450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
            485                 490                 495

Lys Thr Pro Pro Ser Ser Gly Glu Pro Pro Lys Ser Gly Asp Arg Ser
        500                 505                 510

Gly Tyr Ser Ser Pro Gly Ser Pro Gly Thr Pro Gly Ser Arg Ser Arg
            515                 520                 525

Thr Pro
    530

<210> SEQ ID NO 55
<211> LENGTH: 540
<212> TYPE: PRT
<213> ORGANISM: Human

<400> SEQUENCE: 55

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
            85                  90                  95

Ile Pro Glu Gly Thr Thr Ala Glu Glu Ala Gly Ile Gly Asp Thr Pro
        100                 105                 110

Ser Leu Glu Asp Glu Ala Ala Gly His Val Thr Gln Glu Pro Glu Ser
            115                 120                 125

Gly Lys Val Val Gln Glu Gly Phe Leu Arg Glu Pro Gly Pro Pro Gly
        130                 135                 140

Leu Ser His Gln Leu Met Ser Gly Met Pro Gly Ala Pro Leu Leu Pro
145                 150                 155                 160
```

Glu Gly Pro Arg Glu Ala Thr Arg Gln Pro Ser Gly Thr Gly Pro Glu
            165                 170                 175

Asp Thr Glu Gly Gly Arg His Ala Pro Glu Leu Leu Lys His Gln Leu
        180                 185                 190

Leu Gly Asp Leu His Gln Glu Gly Pro Pro Leu Lys Gly Ala Gly Gly
        195                 200                 205

Lys Glu Arg Pro Gly Ser Lys Glu Val Asp Glu Asp Arg Asp Val
    210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
            245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
            275                 280                 285

Val Gly Arg Ala Lys Gly Gln Asp Ala Pro Leu Glu Phe Thr Phe His
            290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
            325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Pro Arg Gly Lys Pro Val
    355                 360                 365

Ser Arg Val Pro Gln Leu Lys Ala Arg Met Val Ser Lys Ser Lys Asp
370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
            405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
            435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
            485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
            515                 520                 525

Thr Pro Ser Leu Pro Thr Pro Thr Arg Glu Pro
    530                 535                 540

<210> SEQ ID NO 56
<211> LENGTH: 550
<212> TYPE: PRT
<213> ORGANISM: Human

<400> SEQUENCE: 56

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Glu Pro Glu Ser
            115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
    195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
    275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430
```

```
Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
    530                 535                 540

Val Val Arg Thr Pro Pro
545             550

<210> SEQ ID NO 57
<211> LENGTH: 560
<212> TYPE: PRT
<213> ORGANISM: Human

<400> SEQUENCE: 57

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255
```

```
Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
                340                 345                 350

Glu Pro Ser Glu Lys Gln Pro Ala Ala Ala Pro Arg Gly Lys Pro Val
            355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
                420                 425                 430

Pro Glu Pro Pro Ser Ser Pro Lys His Val Ser Ser Val Thr Ser Arg
            435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
    515                 520                 525

Thr Pro Ser Leu Pro Thr Pro Pro Thr Arg Glu Pro Lys Lys Val Ala
530                 535                 540

Val Val Arg Thr Pro Pro Lys Ser Pro Ser Ser Ala Lys Ser Arg Leu
545                 550                 555                 560

<210> SEQ ID NO 58
<211> LENGTH: 570
<212> TYPE: PRT
<213> ORGANISM: Human

<400> SEQUENCE: 58

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80
```

```
Asp Glu Gly Ala Pro Gly Lys Gln Ala Ala Gln Pro His Thr Glu
                85                  90                  95
Ile Pro Glu Gly Thr Thr Ala Glu Ala Gly Ile Gly Asp Thr Pro
            100                 105                 110
Ser Leu Glu Asp Glu Ala Ala Gly His Val Thr Gln Glu Pro Glu Ser
        115                 120                 125
Gly Lys Val Val Gln Glu Gly Phe Leu Arg Glu Pro Gly Pro Gly
    130                 135                 140
Leu Ser His Gln Leu Met Ser Gly Met Pro Gly Ala Pro Leu Leu Pro
145                 150                 155                 160
Glu Gly Pro Arg Glu Ala Thr Arg Gln Pro Ser Gly Thr Gly Pro Glu
                165                 170                 175
Asp Thr Glu Gly Gly Arg His Ala Pro Glu Leu Leu Lys His Gln Leu
            180                 185                 190
Leu Gly Asp Leu His Gln Glu Gly Pro Pro Leu Lys Gly Ala Gly Gly
        195                 200                 205
Lys Glu Arg Pro Gly Ser Lys Glu Glu Val Asp Glu Asp Arg Asp Val
    210                 215                 220
Asp Glu Ser Ser Pro Gln Asp Ser Pro Pro Ser Lys Ala Ser Pro Ala
225                 230                 235                 240
Gln Asp Gly Arg Pro Pro Gln Thr Ala Ala Arg Glu Ala Thr Ser Ile
                245                 250                 255
Pro Gly Phe Pro Ala Glu Gly Ala Ile Pro Leu Pro Val Asp Phe Leu
            260                 265                 270
Ser Lys Val Ser Thr Glu Ile Pro Ala Ser Glu Pro Asp Gly Pro Ser
        275                 280                 285
Val Gly Arg Ala Lys Gly Gln Asp Ala Pro Leu Glu Phe Thr Phe His
    290                 295                 300
Val Glu Ile Thr Pro Asn Val Gln Lys Glu Gln Ala His Ser Glu Glu
305                 310                 315                 320
His Leu Gly Arg Ala Ala Phe Pro Gly Ala Pro Gly Glu Gly Pro Glu
                325                 330                 335
Ala Arg Gly Pro Ser Leu Gly Glu Asp Thr Lys Glu Ala Asp Leu Pro
            340                 345                 350
Glu Pro Ser Glu Lys Gln Pro Ala Ala Ala Pro Arg Gly Lys Pro Val
        355                 360                 365
Ser Arg Val Pro Gln Leu Lys Ala Arg Met Val Ser Lys Ser Lys Asp
    370                 375                 380
Gly Thr Gly Ser Asp Asp Lys Lys Ala Lys Thr Ser Thr Arg Ser Ser
385                 390                 395                 400
Ala Lys Thr Leu Lys Asn Arg Pro Cys Leu Ser Pro Lys Leu Pro Thr
                405                 410                 415
Pro Gly Ser Ser Asp Pro Leu Ile Gln Pro Ser Ser Pro Ala Val Cys
            420                 425                 430
Pro Glu Pro Pro Ser Ser Pro Lys His Val Ser Ser Val Thr Ser Arg
        435                 440                 445
Thr Gly Ser Ser Gly Ala Lys Glu Met Lys Leu Lys Gly Ala Asp Gly
    450                 455                 460
Lys Thr Lys Ile Ala Thr Pro Arg Gly Ala Ala Pro Gly Gln Lys
465                 470                 475                 480
Gly Gln Ala Asn Ala Thr Arg Ile Pro Ala Lys Thr Pro Pro Ala Pro
                485                 490                 495
Lys Thr Pro Pro Ser Ser Gly Glu Pro Pro Lys Ser Gly Asp Arg Ser
```

```
                    500                 505                 510
Gly Tyr Ser Ser Pro Gly Ser Pro Gly Thr Pro Gly Ser Arg Ser Arg
                515                 520                 525

Thr Pro Ser Leu Pro Thr Pro Pro Thr Arg Glu Pro Lys Lys Val Ala
            530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu
                565                 570

<210> SEQ ID NO 59
<211> LENGTH: 580
<212> TYPE: PRT
<213> ORGANISM: Human

<400> SEQUENCE: 59

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
```

```
                305                 310                 315                 320
His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Pro Arg Gly Lys Pro Val
        355                 360                 365

Ser Arg Val Pro Gln Leu Lys Ala Arg Met Val Ser Lys Ser Lys Asp
370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
            405                 410                 415

Pro Gly Ser Ser Asp Pro Leu Ile Gln Pro Ser Ser Pro Ala Val Cys
        420                 425                 430

Pro Glu Pro Pro Ser Ser Pro Lys His Val Ser Val Thr Ser Arg
    435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
            485                 490                 495

Lys Thr Pro Pro Ser Ser Gly Glu Pro Pro Lys Ser Gly Asp Arg Ser
        500                 505                 510

Gly Tyr Ser Ser Pro Gly Ser Pro Gly Thr Pro Gly Ser Arg Ser Arg
    515                 520                 525

Thr Pro Ser Leu Pro Thr Pro Pro Thr Arg Glu Pro Lys Lys Val Ala
    530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
            565                 570                 575

Ile Gly Ser Thr
            580

<210> SEQ ID NO 60
<211> LENGTH: 590
<212> TYPE: PRT
<213> ORGANISM: Human

<400> SEQUENCE: 60

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
            85                  90                  95

Ile Pro Glu Gly Thr Thr Ala Glu Glu Ala Gly Ile Gly Asp Thr Pro
```

```
                100                 105                 110
Ser Leu Glu Asp Glu Ala Ala Gly His Val Thr Gln Glu Pro Glu Ser
            115                 120                 125
Gly Lys Val Val Gln Glu Gly Phe Leu Arg Glu Pro Gly Pro Gly
        130                 135                 140
Leu Ser His Gln Leu Met Ser Gly Met Pro Gly Ala Pro Leu Leu Pro
145                 150                 155                 160
Glu Gly Pro Arg Glu Ala Thr Arg Gln Pro Ser Gly Thr Gly Pro Glu
            165                 170                 175
Asp Thr Glu Gly Gly Arg His Ala Pro Glu Leu Leu Lys His Gln Leu
        180                 185                 190
Leu Gly Asp Leu His Gln Glu Gly Pro Pro Leu Lys Gly Ala Gly Gly
            195                 200                 205
Lys Glu Arg Pro Gly Ser Lys Glu Glu Val Asp Glu Asp Arg Asp Val
        210                 215                 220
Asp Glu Ser Ser Pro Gln Asp Ser Pro Pro Ser Lys Ala Ser Pro Ala
225                 230                 235                 240
Gln Asp Gly Arg Pro Pro Gln Thr Ala Ala Arg Glu Ala Thr Ser Ile
            245                 250                 255
Pro Gly Phe Pro Ala Glu Gly Ala Ile Pro Leu Pro Val Asp Phe Leu
        260                 265                 270
Ser Lys Val Ser Thr Glu Ile Pro Ala Ser Glu Pro Asp Gly Pro Ser
            275                 280                 285
Val Gly Arg Ala Lys Gly Gln Asp Ala Pro Leu Glu Phe Thr Phe His
        290                 295                 300
Val Glu Ile Thr Pro Asn Val Gln Lys Glu Gln Ala His Ser Glu Glu
305                 310                 315                 320
His Leu Gly Arg Ala Ala Phe Pro Gly Ala Pro Gly Glu Gly Pro Glu
            325                 330                 335
Ala Arg Gly Pro Ser Leu Gly Glu Asp Thr Lys Glu Ala Asp Leu Pro
        340                 345                 350
Glu Pro Ser Glu Lys Gln Pro Ala Ala Ala Pro Arg Gly Lys Pro Val
            355                 360                 365
Ser Arg Val Pro Gln Leu Lys Ala Arg Met Val Ser Lys Ser Lys Asp
        370                 375                 380
Gly Thr Gly Ser Asp Asp Lys Lys Ala Lys Thr Ser Thr Arg Ser Ser
385                 390                 395                 400
Ala Lys Thr Leu Lys Asn Arg Pro Cys Leu Ser Pro Lys Leu Pro Thr
            405                 410                 415
Pro Gly Ser Ser Asp Pro Leu Ile Gln Pro Ser Ser Pro Ala Val Cys
        420                 425                 430
Pro Glu Pro Pro Ser Ser Pro Lys His Val Ser Ser Val Thr Ser Arg
            435                 440                 445
Thr Gly Ser Ser Gly Ala Lys Glu Met Lys Leu Lys Gly Ala Asp Gly
        450                 455                 460
Lys Thr Lys Ile Ala Thr Pro Arg Gly Ala Ala Pro Pro Gly Gln Lys
465                 470                 475                 480
Gly Gln Ala Asn Ala Thr Arg Ile Pro Ala Lys Thr Pro Pro Ala Pro
            485                 490                 495
Lys Thr Pro Pro Ser Ser Gly Glu Pro Pro Lys Ser Gly Asp Arg Ser
        500                 505                 510
Gly Tyr Ser Ser Pro Gly Ser Pro Gly Thr Pro Gly Ser Arg Ser Arg
            515                 520                 525
```

```
Thr Pro Ser Leu Pro Thr Pro Pro Thr Arg Glu Pro Lys Lys Val Ala
            530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly
                580                 585                 590

<210> SEQ ID NO 61
<211> LENGTH: 600
<212> TYPE: PRT
<213> ORGANISM: Human

<400> SEQUENCE: 61

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320
```

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
    530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp
        595                 600

<210> SEQ ID NO 62
<211> LENGTH: 610
<212> TYPE: PRT
<213> ORGANISM: Human

<400> SEQUENCE: 62

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

```
Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Glu Pro Glu Ser
            115                 120                 125

Gly Lys Val Val Gln Glu Gly Phe Leu Arg Glu Pro Gly Pro Pro Gly
        130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Val Asp Glu Asp Arg Asp Val
                210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
        290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
        370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
        450                 455                 460

Lys Thr Lys Ile Ala Thr Pro Arg Gly Ala Ala Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525
```

```
Thr Pro Ser Leu Pro Thr Pro Pro Thr Arg Glu Pro Lys Lys Val Ala
        530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser
    610

<210> SEQ ID NO 63
<211> LENGTH: 620
<212> TYPE: PRT
<213> ORGANISM: Human

<400> SEQUENCE: 63

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285
```

```
Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
    530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly
    610                 615                 620

<210> SEQ ID NO 64
<211> LENGTH: 630
<212> TYPE: PRT
<213> ORGANISM: Human

<400> SEQUENCE: 64

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45
```

```
Gln Thr Pro Thr Glu Asp Gly Ser Glu Pro Gly Ser Glu Thr Ser
    50                  55                  60

Asp Ala Lys Ser Thr Pro Thr Ala Glu Asp Val Thr Ala Pro Leu Val
65              70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
            115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
            195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
            275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
            355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
            435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
```

```
                   465                 470                 475                 480
            Gly Gln Ala Asn Ala Thr Arg Ile Pro Ala Lys Thr Pro Pro Ala Pro
                            485                 490                 495
            Lys Thr Pro Pro Ser Ser Gly Glu Pro Pro Lys Ser Gly Asp Arg Ser
                        500                 505                 510
            Gly Tyr Ser Ser Pro Gly Ser Pro Gly Thr Pro Gly Ser Arg Ser Arg
                    515                 520                 525
            Thr Pro Ser Leu Pro Thr Pro Pro Thr Arg Glu Pro Lys Lys Val Ala
                530                 535                 540
            Val Val Arg Thr Pro Pro Lys Ser Pro Ser Ala Lys Ser Arg Leu
            545                 550                 555                 560
            Gln Thr Ala Pro Val Pro Met Pro Asp Leu Lys Asn Val Lys Ser Lys
                            565                 570                 575
            Ile Gly Ser Thr Glu Asn Leu Lys His Gln Pro Gly Gly Gly Lys Val
                        580                 585                 590
            Gln Ile Ile Asn Lys Lys Leu Asp Leu Ser Asn Val Gln Ser Lys Cys
                    595                 600                 605
            Gly Ser Lys Asp Asn Ile Lys His Val Pro Gly Gly Gly Ser Val Gln
                610                 615                 620
            Ile Val Tyr Lys Pro Val
            625                 630

<210> SEQ ID NO 65
<211> LENGTH: 640
<212> TYPE: PRT
<213> ORGANISM: Human

<400> SEQUENCE: 65

Met Ala Glu Pro Arg Gln Glu Phe Glu Val Met Glu Asp His Ala Gly
            1               5                   10                  15
            Thr Tyr Gly Leu Gly Asp Arg Lys Asp Gln Gly Gly Tyr Thr Met His
                        20                  25                  30
            Gln Asp Gln Glu Gly Asp Thr Asp Ala Gly Leu Lys Glu Ser Pro Leu
                    35                  40                  45
            Gln Thr Pro Thr Glu Asp Gly Ser Glu Glu Pro Gly Ser Glu Thr Ser
                50                  55                  60
            Asp Ala Lys Ser Thr Pro Thr Ala Glu Asp Val Thr Ala Pro Leu Val
            65                  70                  75                  80
            Asp Glu Gly Ala Pro Gly Lys Gln Ala Ala Ala Gln Pro His Thr Glu
                            85                  90                  95
            Ile Pro Glu Gly Thr Thr Ala Glu Glu Ala Gly Ile Gly Asp Thr Pro
                        100                 105                 110
            Ser Leu Glu Asp Glu Ala Ala Gly His Val Thr Gln Glu Pro Glu Ser
                    115                 120                 125
            Gly Lys Val Val Gln Glu Gly Phe Leu Arg Glu Pro Gly Pro Pro Gly
                130                 135                 140
            Leu Ser His Gln Leu Met Ser Gly Met Pro Gly Ala Pro Leu Leu Pro
            145                 150                 155                 160
            Glu Gly Pro Arg Glu Ala Thr Arg Gln Pro Ser Gly Thr Gly Pro Glu
                            165                 170                 175
            Asp Thr Glu Gly Gly Arg His Ala Pro Glu Leu Leu Lys His Gln Leu
                        180                 185                 190
            Leu Gly Asp Leu His Gln Glu Gly Pro Pro Leu Lys Gly Ala Gly Gly
                    195                 200                 205
            Lys Glu Arg Pro Gly Ser Lys Glu Glu Val Asp Glu Asp Arg Asp Val
```

-continued

```
            210                 215                 220
Asp Glu Ser Ser Pro Gln Asp Ser Pro Pro Ser Lys Ala Ser Pro Ala
225                 230                 235                 240

Gln Asp Gly Arg Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
                275                 280                 285

Val Gly Arg Ala Lys Gly Gln Asp Ala Pro Leu Glu Phe Thr Phe His
290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
                340                 345                 350

Glu Pro Ser Glu Lys Gln Pro Ala Ala Ala Pro Arg Gly Lys Pro Val
                355                 360                 365

Ser Arg Val Pro Gln Leu Lys Ala Arg Met Val Ser Lys Ser Lys Asp
370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
                420                 425                 430

Pro Glu Pro Pro Ser Ser Pro Lys His Val Ser Ser Val Thr Ser Arg
                435                 440                 445

Thr Gly Ser Ser Gly Ala Lys Glu Met Lys Leu Lys Gly Ala Asp Gly
                450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
                500                 505                 510

Gly Tyr Ser Ser Pro Gly Ser Pro Gly Thr Pro Gly Ser Arg Ser Arg
                515                 520                 525

Thr Pro Ser Leu Pro Thr Pro Pro Thr Arg Glu Pro Lys Lys Val Ala
                530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
                580                 585                 590

Gln Ile Ile Asn Lys Lys Leu Asp Leu Ser Asn Val Gln Ser Lys Cys
                595                 600                 605

Gly Ser Lys Asp Asn Ile Lys His Val Pro Gly Gly Gly Ser Val Gln
                610                 615                 620

Ile Val Tyr Lys Pro Val Asp Leu Ser Lys Val Thr Ser Lys Cys Gly
625                 630                 635                 640
```

```
<210> SEQ ID NO 66
<211> LENGTH: 650
<212> TYPE: PRT
<213> ORGANISM: Human

<400> SEQUENCE: 66

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380
```

-continued

```
Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
            405                 410                 415

Pro Gly Ser Ser Asp Pro Leu Ile Gln Pro Ser Ser Pro Ala Val Cys
        420                 425                 430

Pro Glu Pro Pro Ser Ser Pro Lys His Val Ser Ser Val Thr Ser Arg
    435                 440                 445

Thr Gly Ser Ser Gly Ala Lys Glu Met Lys Leu Lys Gly Ala Asp Gly
450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
            485                 490                 495

Lys Thr Pro Pro Ser Ser Gly Glu Pro Pro Lys Ser Gly Asp Arg Ser
        500                 505                 510

Gly Tyr Ser Ser Pro Gly Ser Pro Gly Thr Pro Gly Ser Arg Ser Arg
    515                 520                 525

Thr Pro Ser Leu Pro Thr Pro Pro Thr Arg Glu Pro Lys Lys Val Ala
530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
            565                 570                 575

Ile Gly Ser Thr Glu Asn Leu Lys His Gln Pro Gly Gly Gly Lys Val
        580                 585                 590

Gln Ile Ile Asn Lys Lys Leu Asp Leu Ser Asn Val Gln Ser Lys Cys
    595                 600                 605

Gly Ser Lys Asp Asn Ile Lys His Val Pro Gly Gly Gly Ser Val Gln
610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly
            645                 650

<210> SEQ ID NO 67
<211> LENGTH: 660
<212> TYPE: PRT
<213> ORGANISM: Human

<400> SEQUENCE: 67

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Ala Gly Ile Gly Asp Thr Pro
            100                 105                 110
```

```
Ser Leu Glu Asp Glu Ala Ala Gly His Val Thr Gln Glu Pro Glu Ser
    115                 120                 125

Gly Lys Val Val Gln Glu Gly Phe Leu Arg Glu Pro Gly Pro Pro Gly
130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
    530                 535                 540
```

```
Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
                595                 600                 605

Gly Ser Lys Asp Asn Ile Lys His Val Pro Gly Gly Gly Ser Val Gln
        610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys
            660

<210> SEQ ID NO 68
<211> LENGTH: 670
<212> TYPE: PRT
<213> ORGANISM: Human

<400> SEQUENCE: 68

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255
```

```
Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
    530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly Gly Ser Val Gln
    610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys Leu Asp Phe Lys Asp Arg Val Gln Ser Lys
            660                 665                 670
```

```
<210> SEQ ID NO 69
<211> LENGTH: 680
<212> TYPE: PRT
<213> ORGANISM: Human

<400> SEQUENCE: 69

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
```

```
                385                 390                 395                 400
Ala Lys Thr Leu Lys Asn Arg Pro Cys Leu Ser Pro Lys Leu Pro Thr
            405                 410                 415
Pro Gly Ser Ser Asp Pro Leu Ile Gln Pro Ser Ser Pro Ala Val Cys
            420                 425                 430
Pro Glu Pro Pro Ser Ser Pro Lys His Val Ser Ser Val Thr Ser Arg
            435                 440                 445
Thr Gly Ser Ser Gly Ala Lys Glu Met Lys Leu Lys Gly Ala Asp Gly
            450                 455                 460
Lys Thr Lys Ile Ala Thr Pro Arg Gly Ala Pro Pro Gly Gln Lys
465                 470                 475                 480
Gly Gln Ala Asn Ala Thr Arg Ile Pro Ala Lys Thr Pro Ala Pro
                485                 490                 495
Lys Thr Pro Pro Ser Ser Gly Glu Pro Pro Lys Ser Gly Asp Arg Ser
            500                 505                 510
Gly Tyr Ser Ser Pro Gly Ser Pro Gly Thr Pro Gly Ser Arg Ser Arg
            515                 520                 525
Thr Pro Ser Leu Pro Thr Pro Pro Thr Arg Glu Pro Lys Lys Val Ala
            530                 535                 540
Val Val Arg Thr Pro Pro Lys Ser Pro Ser Ser Ala Lys Ser Arg Leu
545                 550                 555                 560
Gln Thr Ala Pro Val Pro Met Pro Asp Leu Lys Asn Val Lys Ser Lys
                565                 570                 575
Ile Gly Ser Thr Glu Asn Leu Lys His Gln Pro Gly Gly Gly Lys Val
            580                 585                 590
Gln Ile Ile Asn Lys Lys Leu Asp Leu Ser Asn Val Gln Ser Lys Cys
            595                 600                 605
Gly Ser Lys Asp Asn Ile Lys His Val Pro Gly Gly Gly Ser Val Gln
            610                 615                 620
Ile Val Tyr Lys Pro Val Asp Leu Ser Lys Val Thr Ser Lys Cys Gly
625                 630                 635                 640
Ser Leu Gly Asn Ile His His Lys Pro Gly Gly Gly Gln Val Glu Val
                645                 650                 655
Lys Ser Glu Lys Leu Asp Phe Lys Asp Arg Val Gln Ser Lys Ile Gly
            660                 665                 670
Ser Leu Asp Asn Ile Thr His Val
            675                 680

<210> SEQ ID NO 70
<211> LENGTH: 690
<212> TYPE: PRT
<213> ORGANISM: Human

<400> SEQUENCE: 70

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
            20                  25                  30
Gln Asp Gln Glu Gly Asp Thr Asp Ala Gly Leu Lys Glu Ser Pro Leu
        35                  40                  45
Gln Thr Pro Thr Glu Asp Gly Ser Glu Glu Pro Gly Ser Glu Thr Ser
    50                  55                  60
Asp Ala Lys Ser Thr Pro Thr Ala Glu Asp Val Thr Ala Pro Leu Val
65                  70                  75                  80
Asp Glu Gly Ala Pro Gly Lys Gln Ala Ala Ala Gln Pro His Thr Glu
```

```
                    85                  90                  95
Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Glu Pro Glu Ser
            115                 120                 125

Gly Lys Val Val Gln Glu Gly Phe Leu Arg Glu Pro Gly Pro Pro Gly
        130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510
```

-continued

```
Gly Tyr Ser Ser Pro Gly Ser Pro Gly Thr Pro Gly Ser Arg Ser Arg
            515                 520                 525

Thr Pro Ser Leu Pro Thr Pro Pro Thr Arg Glu Pro Lys Lys Val Ala
530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly Gly Ser Val Gln
    610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys Leu Asp Phe Lys Asp Arg Val Gln Ser Lys Ile Gly
            660                 665                 670

Ser Leu Asp Asn Ile Thr His Val Pro Gly Gly Gly Asn Lys Lys Ile
        675                 680                 685

Glu Thr
    690

<210> SEQ ID NO 71
<211> LENGTH: 700
<212> TYPE: PRT
<213> ORGANISM: Human

<400> SEQUENCE: 71

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190
```

```
Leu Gly Asp Leu His Gln Glu Gly Pro Pro Leu Lys Gly Ala Gly Gly
            195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly Gly Ser Val Gln
610                 615                 620
```

```
Ile Val Tyr Lys Pro Val Asp Leu Ser Lys Val Thr Ser Lys Cys Gly
625                 630                 635                 640

Ser Leu Gly Asn Ile His His Lys Pro Gly Gly Gln Val Glu Val
            645                 650                 655

Lys Ser Glu Lys Leu Asp Phe Lys Asp Arg Val Gln Ser Lys Ile Gly
                660                 665                 670

Ser Leu Asp Asn Ile Thr His Val Pro Gly Gly Gly Asn Lys Lys Ile
            675                 680                 685

Glu Thr His Lys Leu Thr Phe Arg Glu Asn Ala Lys
            690                 695                 700

<210> SEQ ID NO 72
<211> LENGTH: 710
<212> TYPE: PRT
<213> ORGANISM: Human

<400> SEQUENCE: 72

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300
```

```
Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
                340                 345                 350

Glu Pro Ser Glu Lys Gln Pro Ala Ala Pro Arg Gly Lys Pro Val
            355                 360                 365

Ser Arg Val Pro Gln Leu Lys Ala Arg Met Val Ser Lys Ser Lys Asp
        370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
                420                 425                 430

Pro Glu Pro Pro Ser Ser Pro Lys His Val Ser Ser Val Thr Ser Arg
                435                 440                 445

Thr Gly Ser Ser Gly Ala Lys Glu Met Lys Leu Lys Gly Ala Asp Gly
                450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
                500                 505                 510

Gly Tyr Ser Ser Pro Gly Ser Pro Gly Thr Pro Gly Ser Arg Ser Arg
                515                 520                 525

Thr Pro Ser Leu Pro Thr Pro Pro Thr Arg Glu Pro Lys Lys Val Ala
                530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
                580                 585                 590

Gln Ile Ile Asn Lys Lys Leu Asp Leu Ser Asn Val Gln Ser Lys Cys
                595                 600                 605

Gly Ser Lys Asp Asn Ile Lys His Val Pro Gly Gly Gly Ser Val Gln
                610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys Leu Asp Phe Lys Asp Arg Val Gln Ser Lys Ile Gly
                660                 665                 670

Ser Leu Asp Asn Ile Thr His Val Pro Gly Gly Gly Asn Lys Lys Ile
                675                 680                 685

Glu Thr His Lys Leu Thr Phe Arg Glu Asn Ala Lys Ala Lys Thr Asp
                690                 695                 700

His Gly Ala Glu Ile Val
705                 710
```

-continued

```
<210> SEQ ID NO 73
<211> LENGTH: 720
<212> TYPE: PRT
<213> ORGANISM: Human

<400> SEQUENCE: 73

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
```

```
                385                 390                 395                 400
Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
    530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly Gly Ser Val Gln
    610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys Leu Asp Phe Lys Asp Arg Val Gln Ser Lys Ile Gly
            660                 665                 670

Ser Leu Asp Asn Ile Thr His Val Pro Gly Gly Gly Asn Lys Lys Ile
        675                 680                 685

Glu Thr His Lys Leu Thr Phe Arg Glu Asn Ala Lys Ala Lys Thr Asp
    690                 695                 700

His Gly Ala Glu Ile Val Tyr Lys Ser Pro Val Val Ser Gly Asp Thr
705                 710                 715                 720

<210> SEQ ID NO 74
<211> LENGTH: 730
<212> TYPE: PRT
<213> ORGANISM: Human

<400> SEQUENCE: 74

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
```

```
                50                    55                    60
Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Ile Gly Asp Thr Pro
                100                 105                 110

Ser Leu Glu Asp Glu Ala Ala Gly His Val Thr Gln Glu Pro Glu Ser
                115                 120                 125

Gly Lys Val Val Gln Glu Gly Phe Leu Arg Glu Pro Gly Pro Gly
130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
                180                 185                 190

Leu Gly Asp Leu His Gln Glu Gly Pro Pro Leu Lys Gly Ala Gly Gly
                195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Pro Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
                260                 265                 270

Ser Lys Val Ser Thr Glu Ile Pro Ala Ser Glu Pro Asp Gly Pro Ser
                275                 280                 285

Val Gly Arg Ala Lys Gly Gln Asp Ala Pro Leu Glu Phe Thr Phe His
                290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
                340                 345                 350

Glu Pro Ser Glu Lys Gln Pro Ala Ala Ala Pro Arg Gly Lys Pro Val
                355                 360                 365

Ser Arg Val Pro Gln Leu Lys Ala Arg Met Val Ser Lys Ser Lys Asp
                370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
                420                 425                 430

Pro Glu Pro Pro Ser Ser Pro Lys His Val Ser Ser Val Thr Ser Arg
                435                 440                 445

Thr Gly Ser Ser Gly Ala Lys Glu Met Lys Leu Lys Gly Ala Asp Gly
                450                 455                 460

Lys Thr Lys Ile Ala Thr Pro Arg Gly Ala Ala Pro Pro Gly Gln Lys
465                 470                 475                 480
```

```
Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
    530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly Gly Ser Val Gln
    610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys Leu Asp Phe Lys Asp Arg Val Gln Ser Lys Ile Gly
            660                 665                 670

Ser Leu Asp Asn Ile Thr His Val Pro Gly Gly Gly Asn Lys Lys Ile
        675                 680                 685

Glu Thr His Lys Leu Thr Phe Arg Glu Asn Ala Lys Ala Lys Thr Asp
    690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser
                725                 730

<210> SEQ ID NO 75
<211> LENGTH: 740
<212> TYPE: PRT
<213> ORGANISM: Human

<400> SEQUENCE: 75

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125
```

-continued

```
Gly Lys Val Val Gln Glu Gly Phe Leu Arg Glu Pro Gly Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430

Pro Glu Pro Pro Ser Pro Lys His Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
    530                 535                 540

Val Val Arg Thr Pro Pro Lys Ser Pro Ser Ser Ala Lys Ser Arg Leu
545                 550                 555                 560
```

```
Gln Thr Ala Pro Val Pro Met Pro Asp Leu Lys Asn Val Lys Ser Lys
                565                 570                 575
Ile Gly Ser Thr Glu Asn Leu Lys His Gln Pro Gly Gly Gly Lys Val
            580                 585                 590
Gln Ile Ile Asn Lys Lys Leu Asp Leu Ser Asn Val Gln Ser Lys Cys
        595                 600                 605
Gly Ser Lys Asp Asn Ile Lys His Val Pro Gly Gly Gly Ser Val Gln
    610                 615                 620
Ile Val Tyr Lys Pro Val Asp Leu Ser Lys Val Thr Ser Lys Cys Gly
625                 630                 635                 640
Ser Leu Gly Asn Ile His His Lys Pro Gly Gly Gly Gln Val Glu Val
                645                 650                 655
Lys Ser Glu Lys Leu Asp Phe Lys Asp Arg Val Gln Ser Lys Ile Gly
            660                 665                 670
Ser Leu Asp Asn Ile Thr His Val Pro Gly Gly Gly Asn Lys Lys Ile
        675                 680                 685
Glu Thr His Lys Leu Thr Phe Arg Glu Asn Ala Lys Ala Lys Thr Asp
    690                 695                 700
His Gly Ala Glu Ile Val Tyr Lys Ser Pro Val Val Ser Gly Asp Thr
705                 710                 715                 720
Ser Pro Arg His Leu Ser Asn Val Ser Ser Thr Gly Ser Ile Asp Met
                725                 730                 735
Val Asp Ser Pro
            740

<210> SEQ ID NO 76
<211> LENGTH: 750
<212> TYPE: PRT
<213> ORGANISM: Human

<400> SEQUENCE: 76

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
            20                  25                  30
Gln Asp Gln Glu Gly Asp Thr Asp Ala Gly Leu Lys Glu Ser Pro Leu
        35                  40                  45
Gln Thr Pro Thr Glu Asp Gly Ser Glu Glu Pro Gly Ser Glu Thr Ser
    50                  55                  60
Asp Ala Lys Ser Thr Pro Thr Ala Glu Asp Val Thr Ala Pro Leu Val
65                  70                  75                  80
Asp Glu Gly Ala Pro Gly Lys Gln Ala Ala Ala Gln Pro His Thr Glu
                85                  90                  95
Ile Pro Glu Gly Thr Thr Ala Glu Glu Ala Gly Ile Gly Asp Thr Pro
            100                 105                 110
Ser Leu Glu Asp Glu Ala Ala Gly His Val Thr Gln Glu Pro Glu Ser
        115                 120                 125
Gly Lys Val Val Gln Glu Gly Phe Leu Arg Glu Pro Gly Pro Pro Gly
    130                 135                 140
Leu Ser His Gln Leu Met Ser Gly Met Pro Gly Ala Pro Leu Leu Pro
145                 150                 155                 160
Glu Gly Pro Arg Glu Ala Thr Arg Gln Pro Ser Gly Thr Gly Pro Glu
                165                 170                 175
Asp Thr Glu Gly Gly Arg His Ala Pro Glu Leu Leu Lys His Gln Leu
            180                 185                 190
```

```
Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
    530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575
```

```
Ile Gly Ser Thr Glu Asn Leu Lys His Gln Pro Gly Gly Lys Val
            580                 585                 590
Gln Ile Ile Asn Lys Lys Leu Asp Leu Ser Asn Val Gln Ser Lys Cys
        595                 600                 605
Gly Ser Lys Asp Asn Ile Lys His Val Pro Gly Gly Gly Ser Val Gln
    610                 615                 620
Ile Val Tyr Lys Pro Val Asp Leu Ser Lys Val Thr Ser Lys Cys Gly
625                 630                 635                 640
Ser Leu Gly Asn Ile His His Lys Pro Gly Gly Gln Val Glu Val
            645                 650                 655
Lys Ser Glu Lys Leu Asp Phe Lys Asp Arg Val Gln Ser Lys Ile Gly
        660                 665                 670
Ser Leu Asp Asn Ile Thr His Val Pro Gly Gly Gly Asn Lys Lys Ile
    675                 680                 685
Glu Thr His Lys Leu Thr Phe Arg Glu Asn Ala Lys Ala Lys Thr Asp
690                 695                 700
His Gly Ala Glu Ile Val Tyr Lys Ser Pro Val Val Ser Gly Asp Thr
            705                 710                 715                 720
Ser Pro Arg His Leu Ser Asn Val Ser Ser Thr Gly Ser Ile Asp Met
                725                 730                 735
Val Asp Ser Pro Gln Leu Ala Thr Leu Ala Asp Glu Val Ser
            740                 745                 750

<210> SEQ ID NO 77
<211> LENGTH: 18
<212> TYPE: PRT
<213> ORGANISM: Human

<400> SEQUENCE: 77

Gln Leu Ala Thr Leu Ala Asp Glu Val Ser Ala Ser Leu Ala Lys Gln
1               5                   10                  15
Gly Leu

<210> SEQ ID NO 78
<211> LENGTH: 28
<212> TYPE: PRT
<213> ORGANISM: Human

<400> SEQUENCE: 78

Thr Gly Ser Ile Asp Met Val Asp Ser Pro Gln Leu Ala Thr Leu Ala
1               5                   10                  15
Asp Glu Val Ser Ala Ser Leu Ala Lys Gln Gly Leu
            20                  25

<210> SEQ ID NO 79
<211> LENGTH: 30
<212> TYPE: PRT
<213> ORGANISM: Human

<400> SEQUENCE: 79

Ser Ser Thr Gly Ser Ile Asp Met Val Asp Ser Pro Gln Leu Ala Thr
1               5                   10                  15
Leu Ala Asp Glu Val Ser Ala Ser Leu Ala Lys Gln Gly Leu
            20                  25                  30

<210> SEQ ID NO 80
<211> LENGTH: 40
<212> TYPE: PRT
<213> ORGANISM: Human
```

-continued

```
<400> SEQUENCE: 80

Asp Thr Ser Pro Arg His Leu Ser Asn Val Ser Ser Thr Gly Ser Ile
1               5                   10                  15

Asp Met Val Asp Ser Pro Gln Leu Ala Thr Leu Ala Asp Glu Val Ser
            20                  25                  30

Ala Ser Leu Ala Lys Gln Gly Leu
            35              40
```